(12) United States Patent
Srivastava et al.

(10) Patent No.: US 11,920,202 B2
(45) Date of Patent: Mar. 5, 2024

(54) UNBIASED IDENTIFICATION OF TUMOR REJECTION MEDIATING NEOEPITOPES

(71) Applicant: University of Connecticut, Farmington, CT (US)

(72) Inventors: Pramod K. Srivastava, Avon, CT (US); Ion I Mandoiu, Storrs, CT (US); Cory A Brennick, Farmington, CT (US); Mariam M George, West Hartford, CT (US); Marmar Moussa, Mansfield Center, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 351 days.

(21) Appl. No.: 17/225,374

(22) Filed: Apr. 8, 2021

(65) Prior Publication Data
US 2021/0317533 A1    Oct. 14, 2021

Related U.S. Application Data

(60) Provisional application No. 63/007,640, filed on Apr. 9, 2020.

(51) Int. Cl.
| | |
|---|---|
| *C12Q 1/6886* | (2018.01) |
| *G01N 33/78* | (2006.01) |
| *G16B 15/30* | (2019.01) |
| *G16B 20/00* | (2019.01) |
| *G16B 35/20* | (2019.01) |
| *G16B 45/00* | (2019.01) |

(52) U.S. Cl.
CPC ........... *C12Q 1/6886* (2013.01); *G01N 33/78* (2013.01); *G16B 15/30* (2019.02); *G16B 20/00* (2019.02); *G16B 45/00* (2019.02); *C12Q 2600/156* (2013.01); *G01N 2800/7028* (2013.01); *G16B 35/20* (2019.02)

(58) Field of Classification Search
USPC .......................................................... 702/20
See application file for complete search history.

(56) References Cited

U.S. PATENT DOCUMENTS

| | | |
|---|---|---|
| 8,140,270 B2 | 3/2012 | Kingsmore et al. |
| 10,055,540 B2 | 8/2018 | Yelensky et al. |
| 10,155,031 B2 | 12/2018 | Sahin et al. |
| 10,426,824 B1 | 10/2019 | Hacohen et al. |
| 10,501,801 B2 | 12/2019 | Srivastava et al. |
| 2009/0098533 A1 | 4/2009 | Munnes et al. |
| 2011/0257890 A1 | 10/2011 | Weinschenk et al. |
| 2011/0293637 A1 | 12/2011 | Hacohen et al. |
| 2012/0093845 A1 | 4/2012 | Tsunoda et al. |
| 2015/0252427 A1 | 9/2015 | Srivastava et al. |
| 2015/0297695 A1 | 10/2015 | Bae et al. |
| 2017/0224799 A1 | 8/2017 | Srivastava et al. |
| 2020/0017922 A1 | 1/2020 | Srivastava et al. |
| 2020/0061168 A1 | 2/2020 | Srivastava et al. |
| 2022/0249634 A1 | 8/2022 | Srivastava et al. |

FOREIGN PATENT DOCUMENTS

| | | | |
|---|---|---|---|
| AU | 2017268822 B2 * | 3/2020 | ............ A61K 35/17 |
| JP | 2014523406 | 9/2014 | |
| WO | 2011143656 A2 | 11/2011 | |
| WO | 2014052707 A2 | 4/2014 | |
| WO | 2012159754 A2 | 11/2016 | |

OTHER PUBLICATIONS

Li, L., S. P. Goedegebuure, and William E. Gillanders. "Preclinical and clinical development of neoantigen vaccines." Annals of Oncology 28 (2017): xii11-xii17. (Year: 2017).*
Duan, Fei, et al. "Genomic and bioinformatic profiling of mutational neoepitopes reveals new rules to predict anticancer immunogenicity." Journal of Experimental Medicine 211.11 (2014): 2231-2248. (Year: 2014).*
Fritsch, Edward F., et al. "HLA-Binding Properties of Tumor Neoepitopes in Humans Tumor Neoepitopes in Humans." Cancer immunology research 2.6 (2014): 522-529. (Year: 2014).*
Assarsson et al.; "A Quantitative Analysis of the Variables Affecting the Repertoire of T Cell Specificities Recognized after Vaccinia Virus Infection"; J Immunol/ 178; pp. 7890-7901; (2007).
Borbulevych, Oleg Y., et al., "Structures of MART-1 26/27~35 Peptide/HLA-A2 Complexes Reveal a Remarkable Disconnect between Antigen Structural Homology and T Cell Recognition", J. Mol. Biol., 2007, and vol. 372, No. 5 and pp. 1123-1136.
Brennick, C. et al.; "An unbiased approach to defining bona fide cancer neoepitopes that elicit immune-mediated cancer rejection"; The Journal of Clinical Investigation, vol. 131, Issue No. 3; 2021; 16 pages; doi: 10.1172/JCI142823.
Castle et al.; "Exploiting the Mutanome for Tumor Vaccination"; Cancer Research; 72(5); pp. 1081-1091; (2012).

(Continued)

*Primary Examiner* — G. Steven Vanni
*Assistant Examiner* — Dylan C Jones
(74) *Attorney, Agent, or Firm* — Nicholas R. Herrel, Esq.; CANTOR COLBURN LLP

(57) ABSTRACT

Described herein is an unbiased method of identifying tumor rejection mediating neoepitopes (TRMNs). Putative neoepitopes from a cancer cell exome sequence from a cancer patient are putative neoepitopes are unbiased by MHC binding and/or CD8T* reactivity. By plotting the putative neoepitope $IC_{50}$s on one axis, and the non-mutated amino acid sequence $IC_{50}$s on a perpendicular axis to provide a bivariate scatter plot, novel TRMNs are identified TRMNs the neoepitopes in the bivariate scatter plot which are in the space greater than 501 nM on the x-axis and greater than 501 nM on the y-axis. Peptides and nucleic acids for expressing peptides including the TRMNs are also described.

13 Claims, 30 Drawing Sheets
(30 of 30 Drawing Sheet(s) Filed in Color)
Specification includes a Sequence Listing.

(56) References Cited

OTHER PUBLICATIONS

Duan et al.; "A mutation in Transportin3 (Tnpo3) leads to generation of an individually distinct tumor-specific Kd-restricted epitope in the Meth A fibrosarcoma (TUM2P.899)"; The Journal of Immunology, vol. 192, Supplement 1, 71.32; 2014; 1 page.
Duan et al.; "Genomic and Bioinformatic Profiling of Mutational Neoepitopes Reveals New Rules to Predict Anticancer Immunogenicity"; J. Exp Med; 211; pp. 2231-2248; (2014).
Ebrahimi-Nik, H. et al.; "CD11c+ MHCIIIo GM-CSF-bone marrow-derived dendritic cells act as antigen donor cells and as antigen presenting cells in neoepitope-elicited tumor immunity against a mouse fibrosarcoma"; Cancer Immunology, Immunotherapy, vol. 67; 2018; pp. 1449-1459.
EP Application 13840946.1 Extended Search Report dated Sep. 2, 2016; 11 pages.
Fortier et al.; "The MHC Class I Peptide Repertoire is Molded by the Transcriptome"; The Journal of Experimental Medicine; 205(3); pp. 595-610; (2008).
Fritsch et al.; "HLA-Binding Properties of Tumor Neoepitopes in Humans"; Cancer Immunology Res.; 2(6); pp. 622-529; (2014).
Ghorani et al.; "Differential Binding Affinity of Mutated Peptides for MHC Class I is a Predictor of Survival in Advanced Lung Cancer and Melanoma"; Annals of Oncology, vol. 29: pp. 271-279; (2017).
Hos, B. et al.; "Identification of a neo-epitope dominating endogenous CD8 T cell responses to MC-38 colorectal cancer"; Oncoimmunology, vol. 9, Issue No. 1; 2020; https://doi.org/10.1080/2162402X.2019.1673125; 11 pages.
International Search Report and Written Opinion; International Application No. PCT/US13/62100; International Filing Date Sep. 27, 2013; dated Jan. 8, 2014; 18 pages.
International Search Report and Written Opinion; International Application No. PCT/US2015/048345; International Filing Date Sep. 3, 2015; dated Dec. 15, 2015; 13 pages.
Jorgensen et al.; "NetMHCstab [ Predicting Stability of Peptide-MHC-1 Complexes; Impacts for Cytotoxic T Lymphocyte Epitope Discovery"; Immunology; 141; pp. 18-26 (2013).
Keskin, et al.; "Neoantigen vaccine generates intratumoral T cell responses in phase lb glioblastoma trial"; Nature, vol. 565, Issue No. 7738; 2019; pp. 234-239.
Knapp, Bernhard; "3-Layer-based analysis of peptide-MHC interaction: In silico prediction, peptide binding affinity and T cell activation in a relevant allergen-specific model", Molecular Immunology, 2009, and vol. 46 and pp. 1839-1844.
Kreiter et al.; "Targeting the Tumor Mutanome for Personalized Vaccinatio Therapy"; OncoImmunology; 1:5; pp. 768-769; (2012).
Martin, S. et al.; "Low Mutation Burden in Ovarian Cancer May Limit the Utility of Neoantigen-Targeted Vaccines"; PLOS One, vol. 11, Issue No. 5; 2016; doi:10.1371/journal.pone.0155189; 22 pages.
Massive Parallel Sequencing from Wikipedia; available under the Creative Commons Attribution_ShareAlike License; 7 pages; https://en.wikipedia.org/w/index.php?title=Massive_parallel_sequencing &oldid=853277093; printed Sep. 2018.
Philip, M. et al.; "Chromatin states define tumor-specific T cell dysfunction and reprogramming"; Nature, vol. 545, Issue 7655; 2017; pp. 452-456.
Priyadarshini, Vani et al., "Genome-based approaches to develop epitope-driven subunit vaccines against pathogens of infective endocarditis", Journal of BiomolecularStructure and Dynamics, Apr. 2014, vol. 32, No. 6, pp.876-889.
Rech et al.; "Tumor Immunity and Survival as a Function of Alternative Neopeptides in Human Cancer"; Cancer Immunology Research, vol. 6, Issue No. 3; pp. 1-12 (2018); Published OnlineFirst Jan. 16, 2018.
Search Report for EP Application 15839204.3; Extended Search Report dated Mar. 27, 2018; 9 pages.
Segal et al.; "Epitope Landscape in Breast and Colorectal Cancer"; Cancer Res; 68(3); pp. 889-892; (2008).
Srivastava et al.; "Modeling the Repertoire of True Tumor-Specific MHC 1 Epitopes in a Human Tumor"; PLoS One; 4; e6094; pp. 1-7 (2009).
Stephens et al.; "The Landscape of Cancer Genes and Mutational Processes in Breast Cancer"; Nature; 486; pp. 100-404; (2012).

\* cited by examiner

| Cluster 1 | | | Cluster 2 | | | Cluster 3 | | |
|---|---|---|---|---|---|---|---|---|
| Peptide # | Gene name | Reference | Peptide # | Gene name | Reference | Peptide # | Gene name | Reference |
| 1 | Sh3rf1 | This study | 4 | Klf3a | This study | 6 | Tpra1 | This study |
| 2 | Fam171b | This study | 9 | Plk1 | This study | 10 | mLama4 | Gubin et al. |
| 3 | Cox6a2 | This study | 11 | mAlg8 | Gubin et al. | 12 | Dpagt1 | Yadav et al. |
| 5 | Oas3 | This study | 17 | Cdc85c (2) | Ebrahimi-Nik et al. | 13 | Reps1 | Yadav et al. |
| 7 | Psma1 | This study | 19 | Gtf2b | Ebrahimi-Nik et al. | 14 | Adpgk | Yadav et al. |
| 8 | Atg9a | This study | | | | 15 | Rpl18 | Hos et al. |
| 16 | Cdc85c (1) | Ebrahimi-Nik et al. | | | | 18 | 1190007I07Rik | Ebrahimi-Nik et al. |
| | | | | | | 20 | Pdpr | Ebrahimi-Nik et al. |

FIGURE 6C

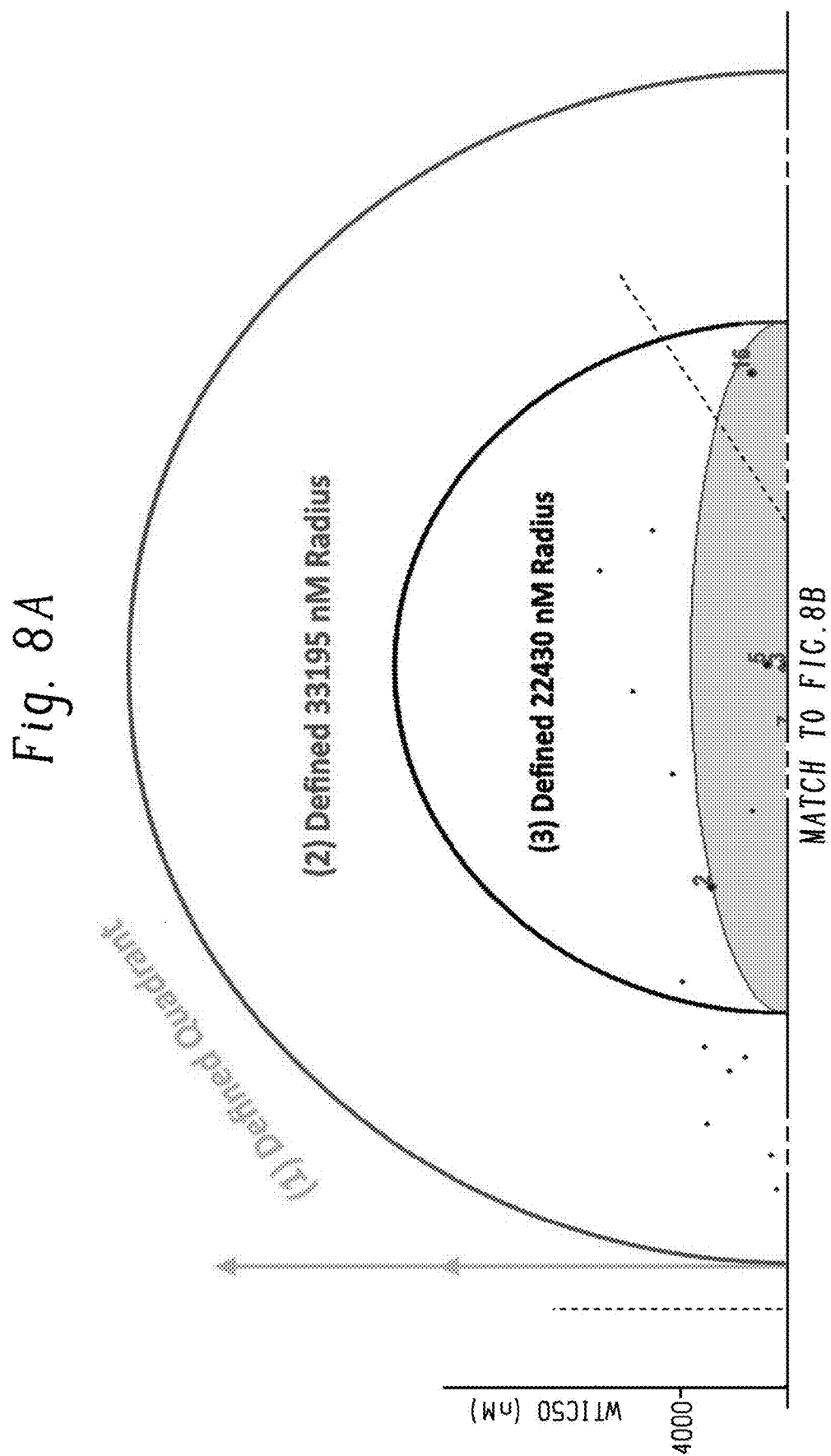

SEQUENCE LISTING

```
<160> NUMBER OF SEQ ID NOS: 23

<210> SEQ ID NO 1
<211> LENGTH: 9
<212> TYPE: PRT
<213> ORGANISM: Mus musculus

<400> SEQUENCE: 1

Ser Lys Gly Lys Pro Pro His Pro Met
1               5

<210> SEQ ID NO 2
<211> LENGTH: 9
<212> TYPE: PRT
<213> ORGANISM: Mus musculus

<400> SEQUENCE: 2

Ser Lys Gly Lys Pro Pro His Pro Arg
1               5

<210> SEQ ID NO 3
<211> LENGTH: 11
<212> TYPE: PRT
<213> ORGANISM: Mus musculus

<400> SEQUENCE: 3

Val Asn Pro Leu His Thr Gly Tyr Glu His Pro
1               5                   10

<210> SEQ ID NO 4
<211> LENGTH: 11
<212> TYPE: PRT
<213> ORGANISM: Mus musculus
```

```
<400> SEQUENCE: 4

Val Asn Pro Leu Pro Thr Gly Tyr Glu His Pro
1               5                   10

<210> SEQ ID NO 5
<211> LENGTH: 11
<212> TYPE: PRT
<213> ORGANISM: Mus musculus

<400> SEQUENCE: 5

Tyr Ala Met Glu Ala Val Lys Gln Cys Ser Ala
1               5                   10

<210> SEQ ID NO 6
<211> LENGTH: 11
<212> TYPE: PRT
<213> ORGANISM: Mus musculus

<400> SEQUENCE: 6

Tyr Ala Met Glu Ala Val Lys Gln Gly Ser Ala
1               5                   10

<210> SEQ ID NO 7
<211> LENGTH: 9
<212> TYPE: PRT
<213> ORGANISM: Mus musculus

<400> SEQUENCE: 7

Val Val Trp Glu Thr Asn Glu Ala Ile
1               5

<210> SEQ ID NO 8
<211> LENGTH: 9
<212> TYPE: PRT
<213> ORGANISM: Mus musculus

<400> SEQUENCE: 8

Val Val Arg Glu Thr Asn Glu Ala Ile
1               5

<210> SEQ ID NO 9
<211> LENGTH: 10
<212> TYPE: PRT
<213> ORGANISM: Mus musculus

<400> SEQUENCE: 9

Pro Val Val Trp Glu Thr Asn Glu Ala Ile
1               5                   10

<210> SEQ ID NO 10
<211> LENGTH: 10
<212> TYPE: PRT
<213> ORGANISM: Mus musculus

<400> SEQUENCE: 10

Pro Val Val Arg Glu Thr Asn Glu Ala Ile
1               5                   10

<210> SEQ ID NO 11
<211> LENGTH: 9
<212> TYPE: PRT
<213> ORGANISM: Mus musculus

<400> SEQUENCE: 11
```

```
Asn Met His Val Arg Lys Cys Lys Leu
1               5
```

<210> SEQ ID NO 12
<211> LENGTH: 9
<212> TYPE: PRT
<213> ORGANISM: Mus musculus

<400> SEQUENCE: 12

```
Asn Met His Val Arg Met Gly Lys Leu
1               5
```

<210> SEQ ID NO 13
<211> LENGTH: 10
<212> TYPE: PRT
<213> ORGANISM: Mus musculus

<400> SEQUENCE: 13

```
Ile Thr Pro Ala Gly Ala Leu Asp Lys Leu
1               5                   10
```

<210> SEQ ID NO 14
<211> LENGTH: 10
<212> TYPE: PRT
<213> ORGANISM: Mus musculus

<400> SEQUENCE: 14

```
His Thr Pro Ala Gly Ala Leu Asp Lys Leu
1               5                   10
```

<210> SEQ ID NO 15
<211> LENGTH: 9
<212> TYPE: PRT
<213> ORGANISM: Mus musculus

<400> SEQUENCE: 15

```
Glu Val Ser Gly Val His Arg Phe Phe
1               5
```

<210> SEQ ID NO 16
<211> LENGTH: 9
<212> TYPE: PRT
<213> ORGANISM: Mus musculus

<400> SEQUENCE: 16

```
Glu Val Ser Gly Val His Gly Phe Phe
1               5
```

<210> SEQ ID NO 17
<211> LENGTH: 9
<212> TYPE: PRT
<213> ORGANISM: Mus musculus

<400> SEQUENCE: 17

```
Ser Thr Phe Leu Tyr Phe Ser Phe Phe
1               5
```

<210> SEQ ID NO 18
<211> LENGTH: 9
<212> TYPE: PRT
<213> ORGANISM: Mus musculus

<400> SEQUENCE: 18

```
Thr Thr Phe Leu Tyr Phe Ser Phe Phe
1               5
```

```
<210> SEQ ID NO 19
<211> LENGTH: 10
<212> TYPE: PRT
<213> ORGANISM: Mus musculus

<400> SEQUENCE: 19

Thr Trp Gln Glu Val Gln Ala Arg Asn Met
1               5                   10

<210> SEQ ID NO 20
<211> LENGTH: 10
<212> TYPE: PRT
<213> ORGANISM: Mus musculus

<400> SEQUENCE: 20

Thr Trp Gln Glu Val Gln Ala Arg Ile Val
1               5                   10

<210> SEQ ID NO 21
<211> LENGTH: 9
<212> TYPE: PRT
<213> ORGANISM: Mus musculus

<400> SEQUENCE: 21

Trp Gln Glu Val Gln Ala Arg Asn Met
1               5

<210> SEQ ID NO 22
<211> LENGTH: 9
<212> TYPE: PRT
<213> ORGANISM: Mus musculus

<400> SEQUENCE: 22

Trp Gln Glu Val Gln Ala Arg Ile Val
1               5

<210> SEQ ID NO 23
<211> LENGTH: 9
<212> TYPE: PRT
<213> ORGANISM: Mus musculus

<400> SEQUENCE: 23

Val His Arg Phe Phe Pro Thr Asn Phe
1               5
```

UNBIASED IDENTIFICATION OF TUMOR REJECTION MEDIATING NEOEPITOPES

CROSS-REFERENCE TO RELATED APPLICATIONS

This application claims priority to U.S. Provisional Application 63/007,640 filed on Apr. 9, 2020, which is incorporated herein by reference in its entirety.

FIELD OF THE DISCLOSURE

The present disclosure is related to novel methods for the identification of tumor rejection mediating neoepitopes (TRMNs).

BACKGROUND

Mutational cancer neoepitopes are the only truly tumor-specific antigens. They are therefore the best candidates for cancer vaccines. However, only a very small proportion of all potential neoepitopes in a tumor are true tumor rejection mediating neoepitopes (TRMNs) and their identification is a major challenge. The current methods for prediction of neoepitopes are based primarily on our understanding of major histocompatibility complex (MHC)-peptide interactions. These rules have been derived from extensive study of viral epitopes and have stood the test of time. However, there is now increasing evidence from human and murine studies that these rules may not apply as neatly to the definition of TRMNs. The clinical trials using neoepitopes have consistently shown that CD4$^+$ T cell responses against immunizing neoantigens identifies using (MHC) class I binding prediction algorithms were detected. Ghorani et al. ("Differential binding affinity of mutated peptides for MHC class I is a predictor of survival in advanced lung cancer and melanoma", *Ann Oncol.* 2018; 29(1):271-279. doi:10.1093/annonc/mdx687) and Rech et al. ("Tumor Immunity and Survival as a Function of Alternative Neopeptides in Human Cancer", *Cancer Immunol Res.* 2018; 6(3):276-287. doi: 10.1158/2326-6066.CIR-17-0559) examined mutational and clinical outcome data from several thousand patients and concluded remarkably that the presence of high affinity MHC-binding neoepitopes in tumors showed no correlation with overall survival, progression-free survival and T cell infiltration in tumors. Previously, Duan et al. ("Genomic and bioinformatic profiling of mutational neoepitopes reveals new rules to predict anticancer immunogenicity", *J Exp Med.* 2014; 211(11):2231-2248. doi:10.1084/jem.20141308) had similarly reported that lack of anti-tumor activity in high affinity MHC I-binding neoepitopes in mouse models. Nelson and colleagues have reported a complete absence of anti-tumor activity among all the high affinity MHC I-binding neoepitopes of a murine ovarian cancer (Martin et al., "Low Mutation Burden in Ovarian Cancer May Limit the Utility of Neoantigen-Targeted Vaccines", *PLOS ONE.* 2016; 11(5):e0155189. doi:10.1371/journal.pone.0155189).

What is needed are novel methods for the identification of true TRMNs.

BRIEF SUMMARY

In an aspect, an unbiased method of identifying tumor rejection mediating neoepitopes (TRMNs) comprises comparing a cancer cell exome sequence from a cancer patient to a reference exome sequence and identifying single nucleotide variants (SNVs) in the cancer cell exome sequence compared to the reference exome sequence; validating the SNVs using nucleic acid sequencing; identifying 8-14 amino acid putative neoepitopes including the validated SNVs, wherein the putative neoepitopes are unbiased by MHC binding and/or CD8T* reactivity; calculating an $IC_{50}$ for an MHC allele for each 8-14 amino acid putative neoepitope including the SNVs, and calculating an $IC_{50}$ for the MHC allele for a corresponding non-mutated amino acid sequence for each SNV; plotting the putative neoepitope $IC_{50}$s on the x-axis, and the non-mutated amino acid sequence $IC_{50}$s on the y-axis to provide a bivariate scatter plot; selecting as TRMNs the neoepitopes in the bivariate scatter plot which are in the space greater than 501 nM on the x-axis and greater than 501 nM on the y-axis; producing a peptide population or a nucleic acid population for expressing the peptide population, the peptide population comprising 15-100 amino acid peptides, the peptides including one or more of the TRMNs; producing a pharmaceutical composition comprising a pharmaceutically acceptable carrier and the peptide population or nucleic acid population; and optionally administering the pharmaceutical composition to the cancer patient.

In another aspect, a method of treating a cancer patient comprises identifying an unbiased population of tumor rejection mediating neoepitopes (TRMNs) by the foregoing method; producing a peptide population or a nucleic acid population for expressing the peptide population, the peptide population comprising 15-100 amino acid peptides, the peptides including one or more of the TRMNs; producing a pharmaceutical composition comprising a pharmaceutically acceptable carrier and the peptide population; and administering the pharmaceutical composition to the cancer patient.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 6A-D show defining TRMNs with novel characteristics. (6A) Scatter plot of the normalized (scaled and centered) values (for every potential precise peptide for each SNV tested) of mutant IC$_{50}$ (nM) on the x-axis vs the WT IC$_{50}$ (nM) on the y-axis. The red diagonal represents equal IC$_{50}$ values for mutant and WT or DAI value of 0 in scale. (6B) Plot shows the Bivariate scatter plot of the normalized reference and mutant IC$_{50}$ values of all the peptides; the TRMNs group in 3 clusters: red circles in cluster 1 (7 peptides), green triangles in cluster 2 (5 peptides) and blue squares in cluster 3 (9 peptides). All non-TRMNs are in grey. Inset: Zoomed in illustration of cluster 3. (6C) Table listing all TRMNs in the 3 clusters. (6D) Plot showing the density of scaled mutant IC$_{50}$ values of all TRMN and non-TRMN neoepitopes of MC38-FABF.

The above-described and other features will be appreciated and understood by those skilled in the art from the following detailed description, drawings, and appended claims.

DETAILED DESCRIPTION

Described herein is a selection method for identifying neoantigens for their use in cancer immunotherapy vaccines that are capable of mediating tumor rejection. The selection method encompasses many more putative neoantigens that are normally overlooked in current neoantigen selection algorithms. Current algorithms only select a small fraction of tumor rejecting neoantigens. The inventors have identified an entire new galaxy of neoantigens that effectively mediate tumor rejection. The novel prediction method is trained on neoantigens known to mediate tumor rejection, and not just the ability to elicit a T cell response (which has been shown to not correlate with tumor rejection). The methods described herein allow rapid identification of neoantigens for the use as personalized cancer immunotherapy on its own or in combination with other modalities currently used in the clinic.

Figure 7A:
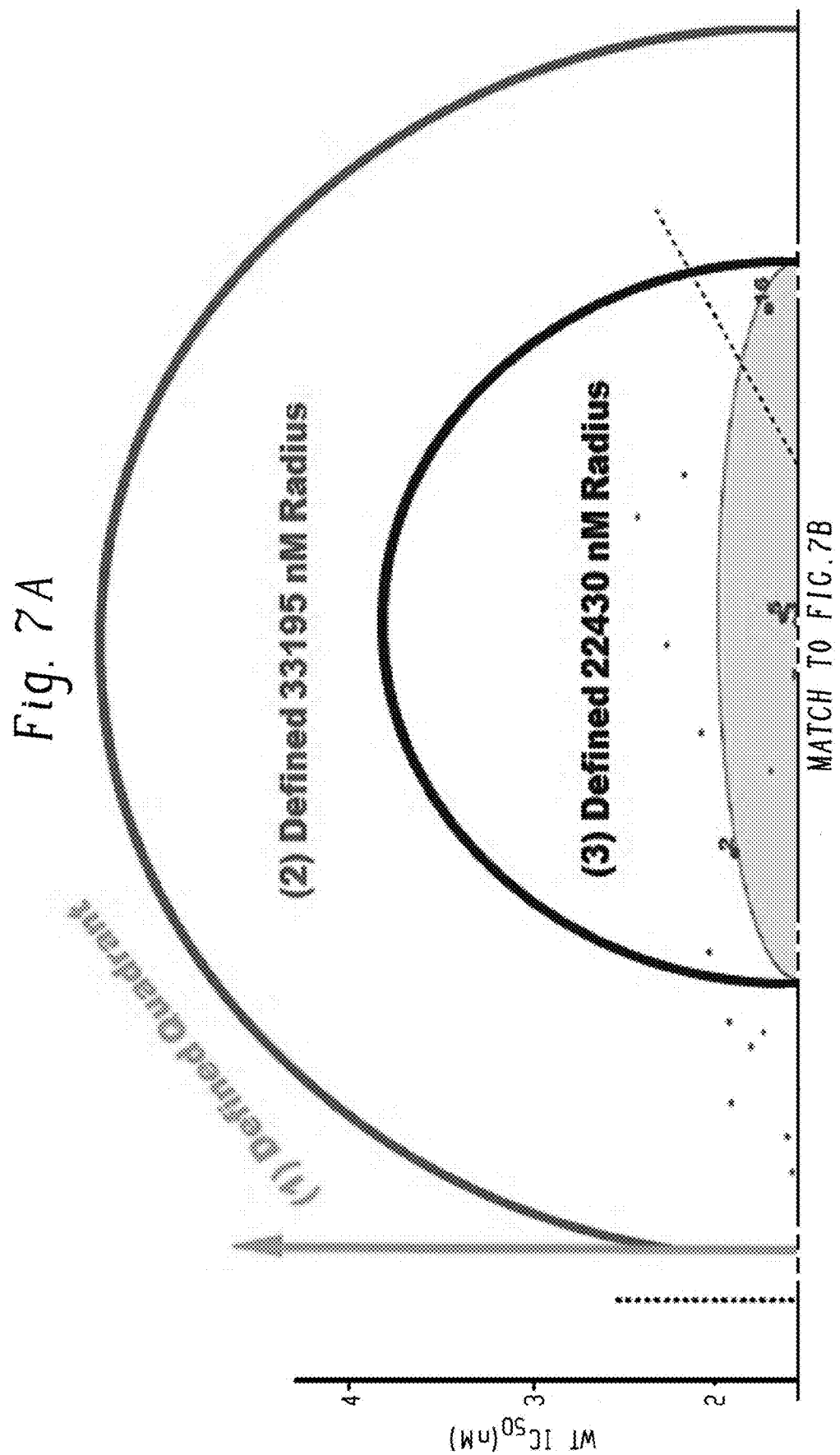
FIGS. 7A and B are a plot showing the overlay of the 3 defined regions of TRMNs on the Bivariate scatter plot from FIG. 6B. Gold represents the defined quadrant where the TRMNs have a binding affinity >501 nM for the mutant and WT $IC_{50}$'s. Orange defines the space surrounding Cluster 1 from FIG. 6B that is defined as having center at 27,176.9 nM and 33,556.51 nM for the x and y axes respectively, and a radius of 33,195 nM from the center while excluding points that have an $IC_{50}$'s<501 nM. Purple defines the space having a center at 27,176.9 nM and 33,556.51 nM for the x and y axes respectively, and a radius of 22,430 nM.
Figure 7B:
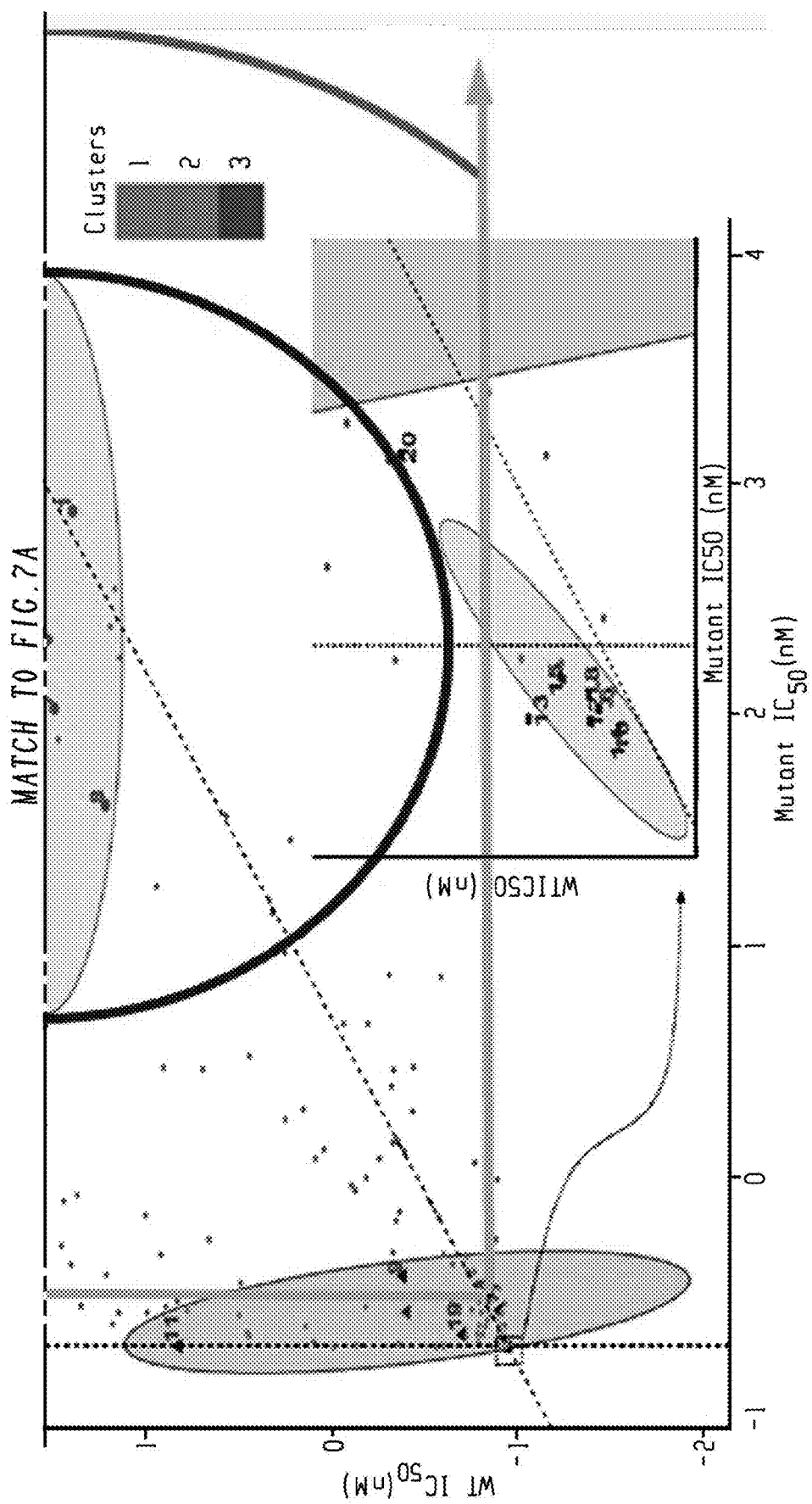
Figure 8B:
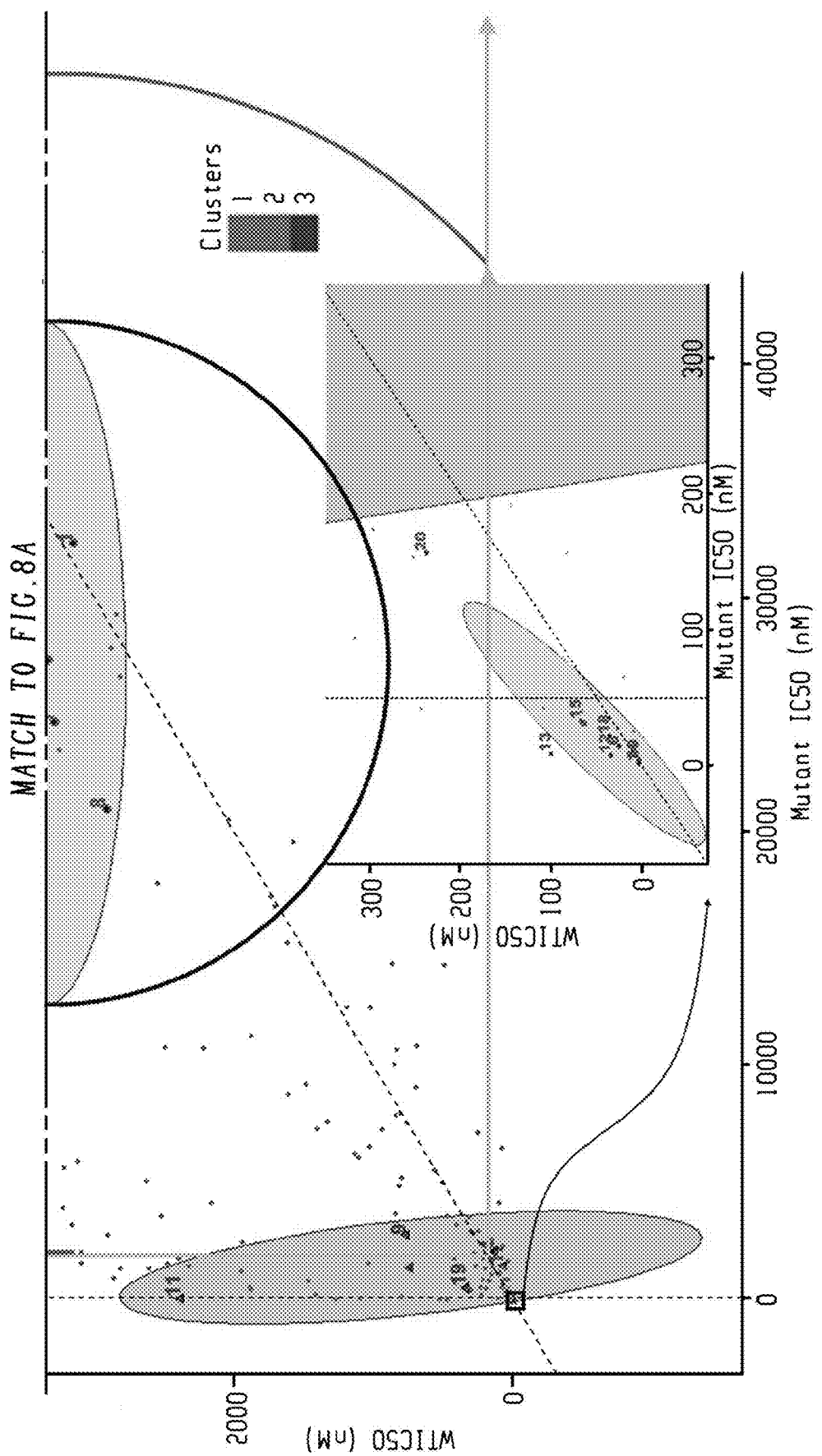
FIGS. 8A and B shows the same plot as FIGS. 7A and B without axis normalization.

More specifically, in a murine model system, the method described herein outperforms current neoantigen selection algorithms, as it identified many more TRMNs than just using a high binding affinity or differential agretopic index (DAI) score alone. Plotting the $IC_{50}$ values of the mutant neoantigen and the corresponding WT peptide on the x and y axes respectively, we define this space bounded by 501 nM on the x-axis and 501 nM on the y-axis as containing new TRMNs, i.e. all points >501 nM in both x and y directions. Specifically, TRMNs are located the space surrounding Cluster 1 from FIG. 6B that is defined as having center at 27,176.9 nM and 33,556.51 nM for the x and y axes respectively, and a radius of 33,195 nM from the center while excluding points that have an $IC_{50}$<501 nM for the mutant and wild type counterparts. Additionally, TRMNs are in the space within Cluster 1 that is defined as having a center at 27,176.9 nM and 33,556.51 nM for the x and y axes respectively, and a radius of 22,430 nM. All defined regions can be seen in FIGS. 7 and 8.

In order to reconcile the conflicting results of the prior art regarding identification of TRMNs, the inventors have queried all possible (nearly 300) neoepitopes using an entirely unbiased approach and asked which of those are effective in mediating tumor rejection, and independently, in eliciting CD8$^+$ T cell response. These analyses reveal unexpected insights into the nature of TRMNs and the rules that may be used to predict them. They show that current methods of prediction discard the majority of true anticancer neoepitopes, and that the true TRMNs have strikingly different properties from epitopes of viral antigens. The identification of a relatively large number of true TRMNs and true non-TRMNs in an unbiased analysis also allows for creation of a preliminary algorithm for prediction of true TRMNs from in silico exome sequencing data.

The study described herein reports an un-biased analysis of the capacity of all confirmed SNVs in a tumor to elicit tumor rejection and CD8$^+$ T cell response. The results generated in one tumor, and validated in another antigenically distinct tumor, challenge two key dogmas in the field and clarify several aspects of the identity and activity of the TRMNs. One dogma is that a high binding affinity MHC I-peptide interaction is a requirement for anti-tumor activity. This dogma is based on established observations that such high affinity (better binding than an $IC_{50}$ value of 50-100 nM) is critical for definition of viral epitopes that elicit CD8$^+$ T cells. The results provided herein show definitively that this is not the case for TRMNs. Nine neoepitopes out of nearly 300 tested, or about 3% of the total, elicited measurable tumor rejection and 8/9 had predicted affinities between $IC_{50}$ values of 2000 nM and 33,000 nM. Two previous studies have reported anti-tumor activity of high affinity neoepitopes, and one previous study has reported the same for low-affinity neoepitopes. A complete absence of anti-tumor activity among all the high affinity MHC I-binding neoepitopes of a murine ovarian cancer has been reported. The study herein reconciles these discordant observations, and vastly expands the universe of TRMNs: using the criterion of high affinity for MHC I, 8/9 TRMNs identified in our study would have been discarded as candidates. These results are supported by the retrospective analyses of the relationship between MHC I-neoepitope affinities and clinical outcomes in human studies. Mutational and clinical outcome data from several thousand patients was examined and it was concluded remarkably that the presence or absence of high affinity MHC-binding neoepitopes in tumors had no correlation with overall survival, progression-free survival and T cell infiltration in tumors, while the presence of low affinity was powerfully correlated with all clinical endpoints in melanoma and lung cancers and in 27 different tumor types.

The second dogma has to do with measurement of CD8$^+$ T cell responses. It is an established fact that CD8$^+$ T cells (among other immune elements) are essential for a successful anti-viral and anti-tumor activity. This fact has generated a dogma: that the CD8$^+$ T cell as measured contemporarily are true surrogate markers of anti-tumor CD8$^+$ activity in vivo. This dogma persists despite the observations in mice and in humans that there is little correlation between measurable CD8$^+$ T cell responses and clinical activity. The tumor immunity elicited by most of the nine TRMNs identified here is CD8$^+$ T cell dependent as observed by the abrogation of immunity by depletion of CD8$^+$ cells as well as by successful adoptive transfer of CD8$^+$ T cells from TRMN-immunized mice to naive mice. Yet, ELISpot, cytotoxicity or FACS assays, the current standards of measurement of CD8$^+$ T cell activity, fail to detect significant CD8$^+$ T cell response to any of these TRMNs. Lower precursor frequencies or tighter regulation of anti-TRMN responses (which are anti-altered-self responses) may contribute to this apparent discrepancy. It is also conceivable that the anti-TRMN CD8$^+$ T cells manifest their anti-tumor activity by mechanisms other than direct action on tumor cells. Development of more sensitive assays such as those based on quantitation of TCR clones may also address this disparity between CD8$^+$ T cell-dependent responses in vivo and lack of a CD8$^+$ T cell response in vitro.

A characteristic of the anti-TRMN CD8$^+$ T cells that can be measured ex vivo is the or stem-like early dysfunctional phenotype. Plasticity of T cells (defined by higher levels of Tcf1 and lower levels of PD1, CD38, CD101, CD39 and TIGIT) has emerged as a significant factor in their function in vivo in viral and tumor models. Without being held to theory, it is believed that the demonstration of such a phenotype in anti-TRMN CD8$^+$ TILs is the first such demonstration in endogenous CD8$^+$ cells in a non-transgenic tumor. The stem-like early dysfunctional phenotype of the anti-TRMNs CD8$^+$ cells may also have a link with the low affinity of TRMNs for MHC I. The low-affinity of TRMNs for MHC I may influence the phenotypes of T cells engaged by pMHC I complexes: (a) During cross-presentation, fewer APCs present the low affinity peptide (as compared to a high affinity peptide), causing T cells to receive a signal through the TCR less frequently, and (b) on an APC that presents the low affinity peptide, there will be fewer pMHCs on the cell surface that contain this peptide, resulting in a relatively lower avidity for T cell recognizing this pMHC on this cell. Both consequences will lead to a less exhausted T cell phenotype.

There are a number of estimates about the frequency of TRMNs among all potential neoepitopes. These estimates, which range from 0.1% to 1% are based on high affinity of neoepitopes for MHC and/or the proportion of neoepitopes against whom a CD8$^+$ T cell response is detected. Since the present study is the only analysis of definition of true TRMNs among all candidate neoepitopes, the conclusion, that TRMNs constitute >3% of candidate neoepitopes, is significant. Since the analysis covers only SNVs and does not take into consideration INDELS and other somatic variations, this number represents an underestimate of the true proportion of TRMNs. These considerations have profound consequences for our aspirations in human cancer immunotherapy.

In an aspect, an unbiased method of identifying tumor rejection mediating neoepitopes (TRMNs) comprises comparing a cancer cell exome sequence from a cancer patient to a reference exome sequence and identifying single nucleotide variants (SNVs) in the cancer cell exome sequence compared to the reference exome sequence; validating the SNVs using nucleic acid sequencing; identifying 8-14 amino acid putative neoepitopes including the validated SNVs, wherein the putative neoepitopes are unbiased by MHC binding and/or CD8T* reactivity; calculating an $IC_{50}$ for an MHC allele for each 8-14 amino acid putative neoepitope including the SNVs, and calculating an $IC_{50}$ for the MHC allele for a corresponding non-mutated amino acid sequence for each SNV; plotting the putative neoepitope $IC_{50}$s on one axis, and the non-mutated amino acid sequence $IC_{50}$s on a perpendicular axis to provide a bivariate scatter plot; and selecting as TRMNs the neoepitopes in the bivariate scatter plot which are in the space greater than 501 nM on the x-axis and greater than 501 nM on the y-axis.

In the first step, a cancer cell exome sequence from a cancer patient is compared to a reference exome sequence and identifying single nucleotide variants (SNVs) in the cancer cell exome sequence compared to the reference exome sequence. Exome sequencing is sequencing the protein-encoding parts of the genome. In an aspect, the cancer cell exome sequence includes all potential neoepitopes in the cancer cells. In another aspect, the reference exome is from a subject of the same species as the cancer cells.

In the second step, the SNVs are validated using nucleic acid sequencing such as by Sanger sequencing.

In the third step, 8-14 amino acid putative neoepitopes including the validated SNVs are identified, wherein the putative neoepitopes are unbiased by MHC binding and/or CD8T* reactivity, preferably the putative neoepitopes are unbiased by MHC binding and CD8T* reactivity. In an aspect, the mutation is roughly at the center of the neoepitope.

In the fourth step, an $IC_{50}$ for an MHC allele is calculated for each 8-14 amino acid putative neoepitope including the SNVs, and an ICs for the MHC allele is calculated for a corresponding non-mutated amino acid sequence for each SNV.

In an aspect, calculating an $IC_{50}$ for an MHC allele comprises determining binding of a peptide to an MHC-allele-specific protein such as K, D or L alleles. One example of such an algorithm is NetMHC-3.2 or NetMHC-4.0 which predicts the binding of peptides to a number of different HLA alleles using artificial neural networks (ANNs) and weight matrices. NetMHC-4.0 uses 81 different human MHC alleles (HLA-A, -B, -C, and -E) and 41 animal alleles. NetMHC produces a list of potential tumor-specific epitopes for this individual mammal, and gives each epitope and $IC_{50}$ and a numerical score.

Figure 6A:
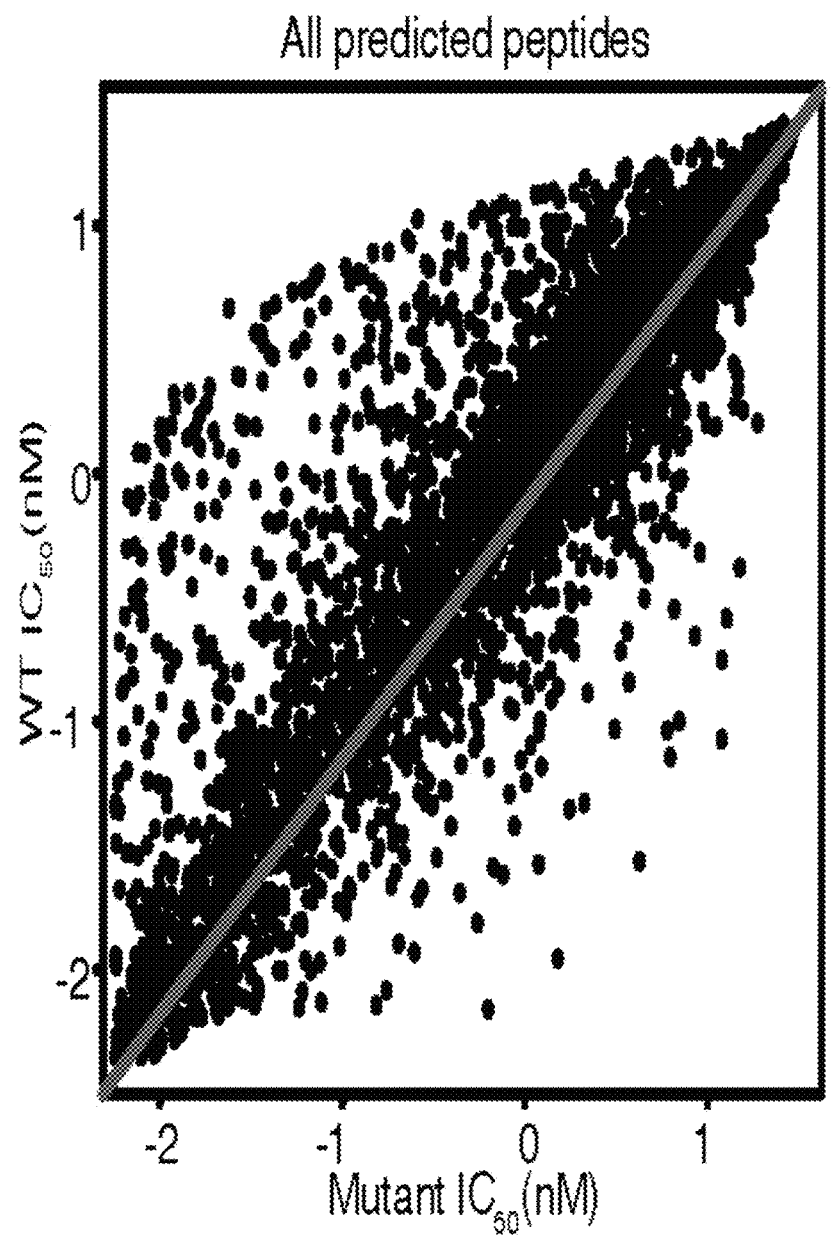
Figure 6B:
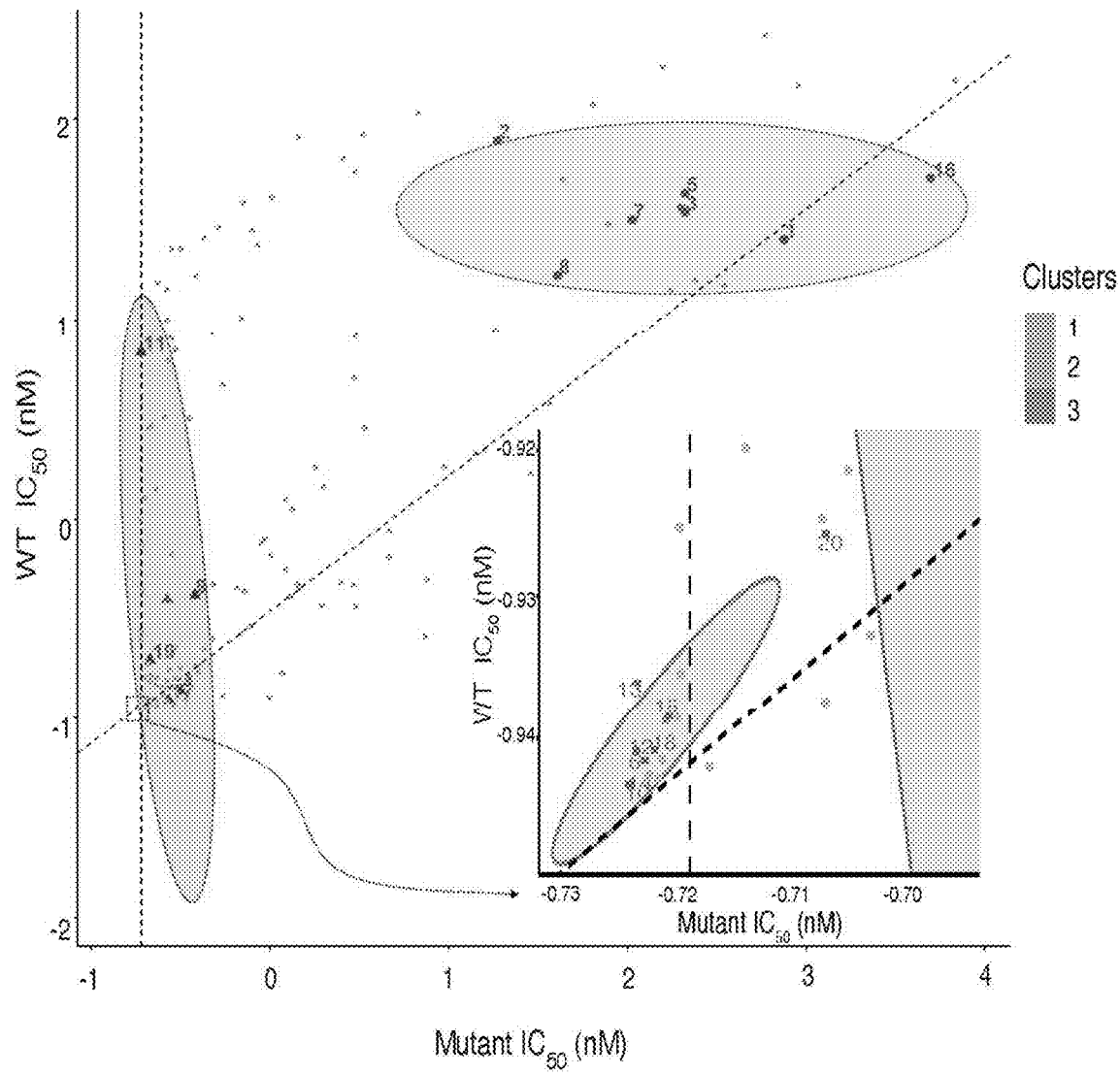

In the fifth step, the putative neoepitope $IC_{50}$s are plotted on the x-axis, and the non-mutated amino acid sequence $IC_{50}$s on the y-axis to provide a bivariate scatter plot. An exemplary scatter plot is shown in FIG. 6B. In an aspect, the method further comprises normalizing the putative neoepitope $IC_{50}$s and the non-mutated amino acid sequence $IC_{50}$s prior to plotting.

In the sixth step, TRMNs are selected as the neoepitopes in the bivariate scatter plot which are in the space greater than 501 nM on the x-axis and greater than 501 nM on the y-axis, i.e. all points >501 nM in both x and y directions.. This space identifies a novel cluster of TRMNs that are normally overlooked. In an aspect, the neoepitopes in the bivariate scatter plot using model-based clustering based on parameterized finite Gaussian mixture models using the $IC_{50}$s. In a specific aspect, the TRMNs are in an elliptical cluster encompassed by the circle having a center at 27,176.9 nM for the x-axis and 33,556.51 nM for the y-axis, and a radius of 33,195 nM from the center. In another specific aspect, the TRMNs are in an elliptical cluster encompassed by the circle having a center at 27,176.9 nM for the x-axis and 33,556.51 nM for the y-axis and a radius of 22,430 nM from the center. These clusters are most highly enriched in TRMNs.

In an aspect, the selected TRMNs have $IC_{50}$ values for the MHC allele of 2000 nM to 33,000 nM.

In another aspect, the selected TRMNs do not produce a statistically significant CD8$^+$ T cell response, measured by ELISpot, cytotoxicity or FACS assays.

Also included herein are isolated TRMN peptide is identified by the methods disclosed herein. An "isolated" or "purified" peptide is substantially free of cellular material or other contaminating polypeptide from the cell or tissue source from which the protein is derived, or substantially free of chemical precursors or other chemicals when chemically synthesized. The language "substantially free of cellular material" includes preparations of polypeptide in which the polypeptide is separated from cellular components of the cells from which it is isolated or recombinantly produced. TRMN peptides generally have lengths of 7 to 25 amino acids, specifically 8 to 15 amino acids, and more specifically 8 to 10 amino acids.

The individual peptides identified as TRMN peptides can be tested for immunogenicity using methods known in the art.

In one embodiment, a peptide corresponding to each TRMN is employed. In another embodiment, a polypeptide containing two or more TRMNs is employed. One polypeptide containing TRMNs optionally separated by non-epitope linkers can be employed. Such polypeptides can be readily designed by one of ordinary skill in the art.

In certain embodiment, instead of TRMN peptides, a pharmaceutical composition comprises one or more polynucleotides encoding the TRMNs. The peptides can all be expressed from the same polynucleotide molecule, or from multiple polynucleotide molecules.

In one aspect, the TRMN peptides contain at least one substitution modification relative to the neo-epitope or one or more nucleotides at the 5'3 or 3' end of the peptide that is not found in the neo-epitope. In another aspect, a detectable label is attached to the TRMN.

"Polynucleotide" or "nucleic acid sequence" refers to a polymeric form of nucleotides at least 5 bases in length. The nucleotides can be ribonucleotides, deoxyribonucleotides, or modified forms of either nucleotide. Polynucleotides can be inserted into a recombinant expression vector or vectors. The term "recombinant expression vector" refers to a plasmid, virus, or other means known in the art that has been manipulated by insertion or incorporation of the peptide genetic sequence. The term "plasmids" generally is designated herein by a lower case "p" preceded and/or followed by capital letters and/or numbers, in accordance with standard naming conventions that are familiar to those of skill in the art. Plasmids disclosed herein are either commercially available, publicly available on an unrestricted basis, or can be constructed from available plasmids by routine application of well-known, published procedures. Many plasmids and other cloning and expression vectors are well known and readily available, or those of ordinary skill in the art may readily construct any number of other plasmids suitable for use. These vectors may be transformed into a suitable host cell to form a host cell vector system for the production of a polypeptide.

The peptide-encoding polynucleotides can be inserted into a vector adapted for expression in a bacterial, yeast, insect, amphibian, or mammalian cell that further comprises the regulatory elements necessary for expression of the nucleic acid molecule in the bacterial, yeast, insect, amphibian, or mammalian cell operatively linked to the nucleic acid molecule encoding the peptides. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns (if introns are present), maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter. By "promoter" is meant minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included.

A pharmaceutical composition (e.g., a vaccine) comprises at least one TRMN peptide (or RNA or DNA encoding a TRMN peptide) and a pharmaceutically acceptable carrier. Pharmaceutically acceptable excipients include, for example, diluents, preservatives, solubilizers, emulsifiers, and adjuvants. As used herein "pharmaceutically acceptable excipients" are well known to those skilled in the art. In one embodiment, a pharmaceutical composition allows for local delivery of the active ingredient, e.g., delivery directly to the location of a tumor.

In specific embodiment, a pharmaceutical composition comprises 1 to 100 immunologically protective TRMN peptides, specifically 3 to 20 TRMN peptides. In another embodiment, a pharmaceutical composition comprises a polypeptide containing 1 to 100 TRMN peptides, specifically 3 to 20 TRMN peptides. In another aspect, a pharmaceutical composition comprises a polynucleotide encoding 1 to 100 TRMN peptides, specifically 3 to 20 tumor-specific TRMN peptides.

In one embodiment, pharmaceutical compositions suitable for intravenous, intramuscular, subcutaneous, intradermal, nasal, oral, rectal, vaginal, or intraperitoneal administration conveniently comprise sterile aqueous solutions of the active ingredient with solutions which are preferably isotonic with the blood of the recipient Such formulations can be conveniently prepared by dissolving the peptide in water containing physiologically compatible substances, such as sodium chloride (e.g., 0.1-2.0 M), glycine, and the like, and having a buffered pH compatible with physiological conditions to produce an aqueous solution, and rendering said solution sterile. These can be present in unit or multi-dose containers, for example, sealed ampoules or vials.

Additional pharmaceutical methods can be employed to control the duration of action. Controlled release preparations can be achieved through the use of polymer to complex or absorb the peptides or nucleic acids. The controlled delivery can be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate a protein, peptides and analogs thereof into particles of a polymeric material, such as polyesters, polyamino acids, hydrogels, polylactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxy-methylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

Local administration to the afflicted site can be accomplished through means known in the art, including, but not limited to, topical application, injection, and implantation of a porous device containing cells recombinantly expressing the peptides, implantation of a porous device in which the peptides are contained.

In one embodiment, the TRMN peptides or polynucleotides are mixed with the cells of the cancer patient, for example, by mixing or pulsing, and then administering the mixed or pulsed cells to the cancer patient.

In one embodiment, a vaccine composition further comprises an immune-modulating agent. Exemplary immune-modulating agents include TLR ligands such, for example, CpG oligonucleotide DNA (a TLR9 ligand), lipopeptides and lipoproteins (TLR1 and TLR2 ligands), poly I:C and double stranded RNA (TLR3 ligands), lipopolysaccharide (TLR4 ligand), diacyl lipopeptide (TLR6 ligands), imiquimod (a TLR7 ligand), and combinations of TLR ligands. Another exemplary immune-modulating agent is an antibody such as anti-cytotoxic T-lymphocyte antigen-4 antibody (anti-CTLA-4), or an antibody blocking Programmed Death 1 (PD1) or a PD1 ligand.

Combinations of immune-modulating agents are also contemplated. Examples are: combination of the vaccine with a TLR ligand and anti-CTLA4 antibody, or with CpG and an antibody blocking PD1.

The immunogenic composition optionally comprises an adjuvant. Adjuvants in general comprise substances that boost the immune response of the host in a non-specific manner. Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel).

In one embodiment a pharmaceutical composition comprises one or more TRMN peptides, one or more polypeptides containing the TRMN peptides, or one or more polynucleotides encoding the one or more TRMN peptides, and a pharmaceutically acceptable carrier, wherein the TRMN peptides do not include epitopes from known cancer-causing pathways.

As used herein, a patient is a mammal, such as a mouse or a human, specifically a human patient.

The compositions and methods described herein are applicable to all cancers including solid tumor cancers, e.g., those of the breast, prostate, ovaries, lungs and brain, and liquid cancers such as leukemias and lymphomas.

The methods described herein can be further combined with additional cancer therapies such as radiation therapy, chemotherapy, surgery, and combinations thereof.

The invention is further illustrated by the following non-limiting examples.

EXAMPLES

Methods

Mice and tumor cell lines: The C57BL/6J (6-8-wk-old females) were purchased from The Jackson Laboratory. A chemically induced murine tumor cell line in the C57BU/6J background known as MC38-FABF was used as the primary tumor model for this extensive study. MC38-FABF tumor cell line was provided by Dr. Alan Frey at NYU Medical Center.

Sample preparation for exome and RNA sequencing and bioinformatic analysis: The exome and transcriptome of the MC38-FABF cell line were sequenced as described in the art. Sequencing was performed following the newer version of the Epi-Seq pipeline. Exome and RNA-Seq reads were aligned to the mm10 mouse reference genome using HISAT2. Single nucleotide variants (SNVs) were called using the somatic variant caller version of SNVQ. The list of SNVs were generated for those mutations with both exome and RNA coverage for each SNV position. The Epitope-Finder tool of Epi-Seq then produced reference and alternative peptide sequences with predicted MHC I binding affinities and Differential Agretope Index (DAI) scores for called SNVs. The DAI is described in U.S. Pat. No. 10,501, 801, incorporated herein by reference for its description of the DAI. Gene expression estimation from RNA-seq data was performed by using IsoEM2 algorithm.

Peptide synthesis: Peptides were custom made with a purity of >90% (JPT, Berlin, Germany and Genscript, Piscataway, NJ) and dissolved in dimethyl sulfoxide (DMSO) at a final concentration of 20 mM.

Generation of BMDCs and neoepitope vaccine preparation: BMDCs were generated by methods known in the art and were pulsed with 100 μM of peptide for approximately 2 hours at 37° C. then washed and resuspended in RPMI 1640.

Immunization with neoepitopes and tumor challenge: For prophylactic immunization, mice were immunized as described. Anti-CTLA-4 antibody was continued every 3 days until termination of the experiment Mice were challenged with 30,000 tumor cells i.d. Tumor volumes were measured using the Biopticon TumorImager™. Tumor Control indices were calculated for every experiment as described in the art. For therapeutic immunization, mice were challenged as above, and then immunized as before on Day 0 or Day 10 post tumor challenge along with anti-CTLA-4 (75 ug/mouse, clone 9D9, Bioxcell). A second immunization and anti-CTLA-4 antibody was administered 7 days later. Anti-CTLA-4 antibody was continued every 3 days until termination of the experiment.

Intracellular IFN-γ assay by ELISpot: As targets to stimulate the $CD8^+$ cells, naive splenocytes pulsed with peptide were added to the wells. Plates were analyzed by ZellNet™. The magnitude of responses was rated by mean spot numbers per million $CD8^+$ cells: 5-10(+); 11-20 (++); 21-50 (+++); 51-100(++++); and >100(+++++).

Depletion of T cell subsets: $CD8^+$ cells were depleted using anti-CD8a rat IgG2b monoclonal antibody 2.43 (Bioxcell). CD4 cells were depleted using anti-CD4 rat IgG2b monoclonal antibody GK1.5 (Bioxcell). Depleting antibodies were given in PBS intraperitoneally (i.p) one day before each immunization at 250 pg per mouse. Depletion was continued every 7 days for the duration of the experiment at 150 pg per mouse. The antagonistic antibody, anti-CTLA-4 (clone 9D9; Bioxcell) was given at 75 pg, 7 days before and every 3 d after tumor challenge. The appropriate T cell subsets were depleted by >95%.

Flow Cytometry: The antibodies for CD8a PacificBluem (clone 53-6.7), CD8a APC-Cy 7 (clone 53-6.7), CD44 Brilliant violet (Clone IM7), PD-1 PCP-Cy5.5 (Clone RMP1-30), PD-1 APC (Clone RMP1-30), Tim3 APC (Clone RMT3-23), Tim3 PCP-Cy5.5 (Clone RMT3-23), ag3 PE/Cy 7 (clone eBioC9B7W) and CD62L APC-Cy7 (Clone MEL-14), CD38 APC (clone 90), CD38 PE/Cy7 (clone 90) were purchased from Biolegend™. The antibody for 2B4 PE-Cy7 (Clone eBio244F4), 2B4 FITC (Clone eBio244F4) and TIGIT PCP-efluor 710 were purchased from ThermoFisher™. The antibody for TCF1 Alexa Fluor® 488 (Clone C63D9), TCF1 PE (Clone C63D9) was purchased from Cell Signaling™. For RMA-S experiments, antibodies for $H2-K^b$ APC (Clone AF6-88.5.5.3) and $H2-D^b$ PE (Clone 28-14-8) was purchase from Thermofischer. Flow cytometry was performed using Miltenyi Biotec MACSQuant® analyzer. Analysis was done using FlowJo software (FlowJo LLC).

MHC I stabilization on RMA-S cells: Precise peptides of the TRMNs identified in FIG. 3A were tested for their ability to bind H2-$K^b$ or H2-$D^b$ using RMA-S cells. RMA-S cells were cultured with the precise peptides at various concentrations at 37° C. for 1 hour. The level of $K^b$ or $D^b$ complexes were tested by flow cytometry.

Molecular modeling and dynamics of peptide/MHC complexes: Structural modeling was performed as previously published. Briefly, Rosetta was used via PyRosetta to model 10,000 structures of both WT and neoepitope peptide-MHC complexes for FAM171b, COX6a2, and SH3RF1 from template structures PDB 1G7P, 2VAB, and 4PGE, respectively. Principal component (PC) analysis was conducted on peptide-only cartesian coordinates of all 10,000 decoys for each peptide modeled, and PC 1-3 were clustered with the density-based spatial clustering of applications with noise (DBSCAN) algorithm using F of 1.5 and a minimum cluster size of 40. From the most populous non-noise cluster, the model with the lowest ref2015 score was retained as a representative model for subsequent evaluation and comparison. Root-mean-square deviation of atomic positions (RMSD) of peptide common or backbone heavy atoms between wild-type and mutant peptides were calculated, and models were inspected visually for differences in structural features with PyMOL or Discovery Studio. Peptide solvent-accessible surface area (SASA) and hydrophobic SASA (hSASA) in the context of the MHC I were calculated in Rosetta with a probe radius of 1.4 Å.

Molecular dynamics simulations were performed as described previously. Briefly, simulations were performed with GPU-accelerated AMBER 18 and the ff14SB force field with the final models for each peptide/MHC from Rosetta used as starting coordinates. Systems were brought to a NaCl concentration of 0.150 M and solvated in explicit SPC/E water with box edges a minimum of 15 Å from protein atoms. A 12 Å cutoff was used for non-bonded interactions. These were brought to local energy minima, heated to 300K under restraints, then equilibrated in an NPT ensemble with stepwise relaxation of restraints. After a final equilibration in an NVT ensemble, production simulations were conducted in an NVT ensemble for 300 ns. Root mean square deviations (RMSD) and root mean square fluctuations (RMSF) of atomic coordinates, as well as ensemble-average structures were calculated with cpptraj utility in AmberTools. Electrostatic surface potentials were calculated using pdb2pqr and APBS with grid spacing of 0.25 Å at a temperature of 310K and salt concentration of 0.150 M.

Isolation of MHC-presented peptides from cells for Mass Spectrometry: MHC I-β2-microglobulin-peptide complexes were isolated from $10^9$ BMDCs pulsed with the 100 μM 21mer peptides, as described in the art. After 1 h incubation, cells were washed with ice-cold PBS, and pellets frozen at −20° C. The frozen pellet was resuspended in ice-cold lysis buffer (20 mM Tris HCl, 150 mM NaCl, 1% Triton™ X-100, 0.1% octyl glucoside, and protease inhibitor cocktail) and incubated for 30 min at 4° C. Lysate was centrifuged at 12,000 g for 20 min at 4° C., and loaded onto a protein G Sepharose column (without bound antibodies) to remove any existing immunoglobulins. The cleared lysate immediately loaded into the prepared protein G Sepharose with covalently bound anti-MHC antibody. This column was incubated for 1 hour at 4° C. The column was washed with 10 mL of buffer A (20 mM Tris HCl, 150 mM NaCl) followed by 10 mL of buffer B (20 mM Tris HCl, 400 mM NaCl), then 10 mL of buffer A again, and lastly 10 mL of buffer C (20 mM Tris HCl). Bound MHC I-$β_2$-microglobulin-peptied complexes were eluted in 0.5 mL fractions using 0.1 N acetic acid.

Eluted proteins were separated from peptides on a Sep-Pak® cartridge. The cartridge was washed with 80% acetonitrile in 0.1% TFA and two additional times with 0.1% TFA. The eluates were applied and the column was washed with 0.1 TFA. Peptides were eluted in 30% acetonitrile in 0.1% TFA, while MHC I and 02-microglobulin, were eluted in subsequently in 80% acetonitrile in 0.1% TFA. The peptides were vacuum dried at 37° C. and stored at −20° C.

MHC-bound peptide analysis using ultra-high performance liquid chromatography and high resolution tandem mass spectrometry: Dried, desalted peptides were resuspended in 0.1% formic acid in water and analyzed using nanoflow ultra-high performance liquid chromatography coupled to tandem mass spectrometry (MS/MS). One microliter of desalted peptides was loaded on a 75 μm×25 cm Easy Spray™ PepMap™ C18 analytical column (Thermo Scientific) held at 35° C. and subject to a 1 hr, 300 nL/min flow linear gradient. Gradient conditions were as follows: 4% Solvent B hold for 10 min, ramp to 30% Solvent B in 40 min, 30% Solvent B to 90% Solvent B in 10 min (Solvent A: 0.1% formic acid in water, Solvent B: 0.1% formic acid in acetonitrile) on a Dionex™ UltiMate™ RSLCnano UPLC system. Eluted peptides were directly ionized into a Q Exactive™ HF hybrid mass spectrometer (Thermo Scientific) using electrospray ionization and a +1.9 kV spray voltage.

The Q Exactivem HF was operated in positive mode and implemented a data-dependent acquisition method comprised of a single full MS scan followed by 15 MS/MS scans. Full MS scans used the following parameters: mass range 300 to 1800 m/z, 60,000 resolution, default charge state 2, 1 microscan, 1e6 AGC target. Data-dependent MS/MS scans used the following parameters: 1 microscan, 15,000 resolution, 1e5 AGC target, maximum IT of 40 ms, 2.0 m/z isolation window, 0.0 m/z isolation offset, normalized collision energy of 27, and dynamic exclusion set to 30 s.

Bioinformatic identification of peptide sequences analyzed using Byonic™: Byonic™ v3.1 (Protein Metrics Inc.) was used to search the raw mass spectrometry data against a custom proteome database comprised of the Uniprot *Mus musculus* proteome (UP000000589, Accessed May 16, 2017) and manually added peptide sequences of the 21mer TRMN-containing peptides that were pulsed onto BMDCs. The common proteomics contaminants Byonic™ database and decoy database were also searched. The following parameters were used: non-specific enzyme specificity, 5 ppm precursor and 20 ppm fragment mass tolerances, oxidized Met and N-terminal acetyl variable modifications, 2,000 Da maximum precursor mass, compute precursor and charge assignments from MS1, automatic score cut (5% peptide spectrum match (PSM) false discovery rate (FDR) cuts) enabled, and no protein level FDR cuts. All other parameters were kept at default values. The Byonic™-reported peptide hits were manually exported from Byonic™ Viewer and sorted by FDR 1D to identify pulsed peptide sequences ranked below 5% PSM FDR. The peptide hit for pulsed BMDC sequence EVSGVHRFF exceeded the PSM FDR cutoff (score 147.6, 0.015 FDR 1D, 0.0085 FDR 2D) and was subject to visual inspection. To increase confidence of the identification, the MS/MS spectrum matched to EVSGVHRFF was then compared to that for a synthetic peptide with identical sequence using the UPLC-MS/MS methods described above.

Isolation of TILs: Tumors were harvested and dissociated using Miltenyi™ Tumor Dissociation Kit, mouse. CD8+ TIL were isolated with STEMCELL's EasySep™ murine CD8 negative selection kit.

Single-Cell RNA Sequencing Library Generation: Single cells were then captured for subsequent single cell RNA sequencing and libraries preparation as follows: 12,000 single cells were loaded for capture using a Chromium Single Cell 5' v1.0 (10× Genomics). Following capture and lysis, cDNA was synthesized and amplified (12 cycles) as per the manufacturer's protocol. The amplified cDNA was then divided and used to construct 3 gene expression libraries and 3 V(D)J T cell enriched libraries as per the manufacturer's protocol. All libraries were sequenced on a Next-Seq™ 550 system (Illumina®) following 10× Genomics suggested read length and depth. The Cell Ranger Single-Cell Software Suite v.3 (10× Genomics) was used to perform sample demultiplexing, barcode processing and single-cell 5' counting.

Single-Cell RNA Sequencing Alignment, Barcode Assignment, and UMI Counting: Cell Ranger v.3 count pipeline was used to process the FASTQ files for each sample. The mm10 genome and transcriptome were used to align samples, filter and quantify. The cellranger aggr pipeline was used to aggregate the analysis files for each sample into a combined set by performing between-sample normalization (samples are subsampled for an equal number of confidently mapped reads per cell). Cell Ranger pipeline output, the 'feature (gene) vs cell' count matrix is then used for the secondary scRNA-Seq analysis in SC1 as described below.

Preprocessing Analysis: Following the SC1 pipeline for scRNA-Seq analysis, secondary QC (quality control) was applied to the combined dataset of balanced number of cells per library (constructed by randomly sampling approximately 5000 cells from each library before QC). Genes that were expressed in less than 10 cells were excluded from the analysis, also to reduce outliers, cells that expressed less than 500 and more than 6000 genes were excluded. Other QC metrics include examining the fraction of reads mapping to mitochondrial genes, cells were excluded if more than 30% of their UMI counts were from mitochondrial genes, and cells with less than 5% of counts in ribosomal protein genes were also excluded. Filtered and log transformed (log 2(x+1)) count matrix was used in Principle Component Analysis (PCA) and the first 50 principle components were used as input for t-SNE dimensionality reduction algorithm to obtain a three-dimensional representation of the cells used for the 3D visualization plots.

Clustering and Cluster Annotation: Most informative genes for clustering were picked by their high average TF-IDF scores as described in the art; hierarchical clustering algorithm using Ward linkage and top average TF-IDF scoring genes as features was used to identify 8 clusters. The top average TF-IDF genes were also used as features for PCA analysis followed by t-SNE projection analysis for the 3D t-SNE dataset representation. To characterize clusters, Differential Expression (DE) analysis was done by One vs. the Rest t-tests (with Welch/Satterthwaite approximation and 0.95 confidence interval) for each cluster using the t-test available in R stats package. We also compared the differentially expressed genes for effector clusters (C3, C5 and C8) vs. C2 and effector/exhausted clusters (C1, C4 and C6) vs. C2, for which the full list of DE genes are provided in supplementary data S3 and S4. All DE analyses use Log2 Fold Change cutoff of 2 and the p-value cutoff of 0.01. Functional enrichment analysis was performed using the 'gProfileR' R package to inform cluster annotation. Cluster stability was evaluated using the Dunn Index, a metric for evaluating clustering algorithms aiming to evaluate compactness of the clustering. The Dunn Index showed a value of 0.6297628 (data not shown). We also evaluated the cluster separation matrix, which includes the separation values between all pairs of clusters, where the separation is defined as the vector of cluster wise minimum distances of a point in the cluster to a point of another cluster. This analysis shows that clusters are well-separated from one another.

TCR sequencing analysis: Specificity groups/clusters in the TCR repertoire were identified via computational analysis following the GLIPH (grouping of lymphocyte interactions by paratope hotspots) algorithm which searches for global and local motif CDR3 similarity in TCR CDR regions with high contact probability. Each specificity group is analyzed in GLIPH for enrichment (of common V-genes, CDR3 lengths, clonal expansions, motif significance, and cluster size. Global similarity measures CDR3 differing by up to one amino acid and local similarity measures the shared enriched CDR3 amino acid motifs with >10× fold-enrichment and probability less than 0.001.

Clustering analysis of Mutant and WT $IC_{50}$ values: For normalization, simple centering and scaling is performed for the WT and mutant $IC_{50}$ sets. Centering is done by subtracting the column means then scaling is done by dividing the (centered) values by their standard deviations. Using the scaled and centered WT and mutant $IC_{50}$ values of all tested FABF peptides and peptides from published works as Features, 3 clusters/ellipses were fitted using Model-based clustering based on parameterized finite Gaussian mixture models from the MClust package in R; the number of clusters was determined by analyzing the Bayesian information criterion (BIC). Top models based on the BIC criterion were VVI at 3 Clusters, with BIC value 21.727154 and VEI, also at 3 clusters with BIC value 7.150494.

Data availability: Single cell data used in this paper is provided as a publicly accessible dataset. Single cell RNA-Seq data of this paper has been submitted to GEO with accession number GSE162432.

Code availability: SC1 tool used for single cell-RNA Seq analysis in this paper is publicly available. Custom code for the TCR analysis and cluster analysis of TRMNs (FIG. 4) is available upon request and deposited on GitHub.

Statistics: P-values for group comparisons were calculated using a two-tailed nonparametric Mann-Whitney test, using GraphPad Prism 5.0 (GraphPad). Fisher's exact test was used to test association between pairs of categorical parameters. Statistical significance of a Pearson correlation coefficient was computed using two-tailed student's t test. Statistical significance of a Pearson correlation coefficient was computed using 2way ANOVA Sidak's multiple comparisons test. Statistical analysis on percent survival curves was conducted using the log rank (Mantel-Cox) test. P values of <0.05 were considered significant. Tukey's multiple comparisons test was done when multiple comparisons were made.

Figure 1A:
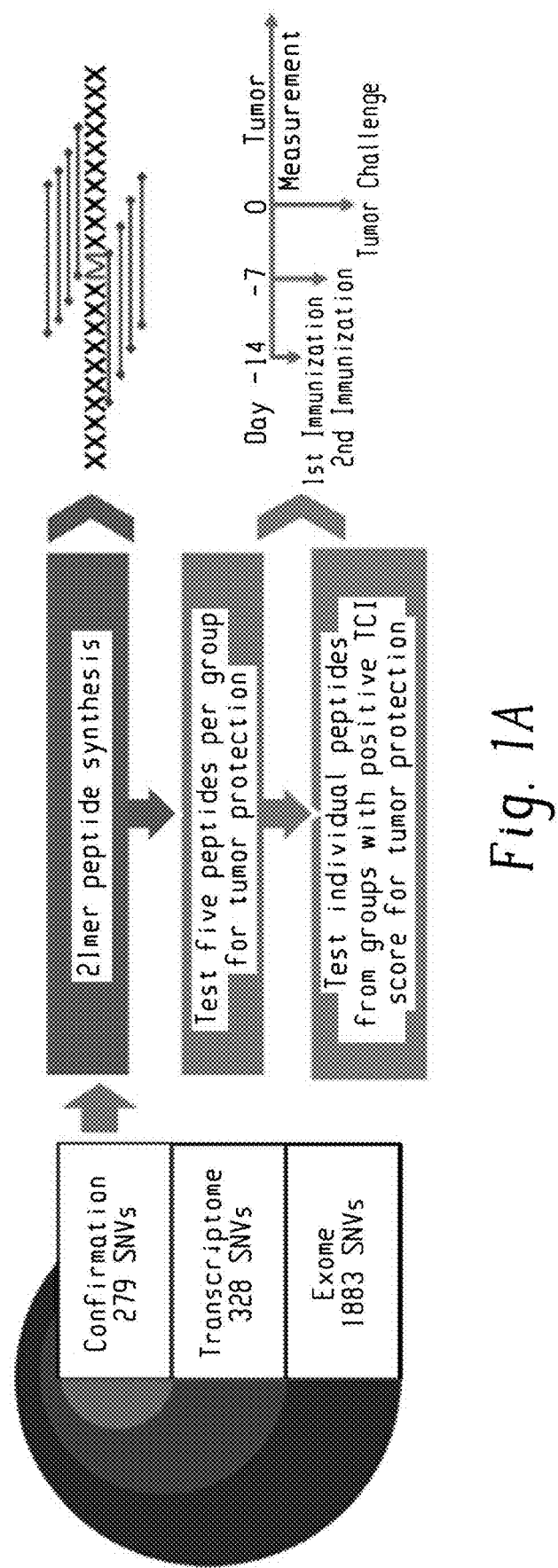
FIGS. 1A-C show unbiased identification of TRMNs. (1A) All experimentally confirmed SNVs of the MC38-FABF tumor, and screening strategy for tumor rejection. (1B) Bar graph representing the tumor control index (TCI) scores (9) for the 58 of all 279 peptides, represented by numbers on the X axis. The remaining 221 peptides elicited no tumor control and are not shown. The negative control (extreme left) consists of mice immunized with un-pulsed BMDCs. Peptides which elicited significant tumor control are marked by asterisks. P and T indicate activity in prophylaxis and therapy. Combination of nine positive peptides (TRMNs) is on the extreme right. The $IC_{50}$ values for peptide-MHC I ($K^b/D^b$), were predicted using NetMHC4.0; the values represent the highest predicted binder for each SNV or an experimentally verified precise neoepitope. Peptides are color coded by $IC_{50}$ values as indicated in the box. n=5-15 mice/group, except for the nine active peptides (TRMNs), for which n=20-50 mice per peptide. All peptides were tested at least three times; the nine active peptides (TRMNs) were tested between four and eight times each. (1C) CD8$^+$ (IFNγ ELISpot) responses to peptides from (1B) in MC38-FABF immunized (blue bars) or naive mice (red bars) (n=4 mice/group). To generate the box and whisker plots, data from every single mouse were entered. The box extends from the 25th to 75th percentiles, the middle line represents the median in each group, and the "+" represents the mean. The whiskers extend from the minimum to maximum value. Statistical analysis was conducted for peptides' response against wells with no target. All peptides were tested at least two times. (1B-C) Means±s.d. shown; Statistical analysis was conducted using student's t test (1B) or 2 way ANOVA (1C).

Example 1: Identification of Single Nucleotide Variants and TRMNS in MC38-FABF Tumor The exome sequences from a murine colon cancer line MC38-FABF (C57BL/6J) were compared with the reference C57BL6/J exome, and 1883 single nucleotide variants (SNVs) were identified (FIG. 1A and data not shown). Of these, genes expressing 328 SNVs were detected in the tumor transcriptome. Of these, 279 SNVs (85%) were validated by Sanger sequencing. For an unbiased analysis of the anti-tumor activity and CD8+ immunogenicity of every validated SNV, 279 peptides were synthesized. The peptides were 21 amino acids long, with the mutation at the center of the peptide, so as to include all putative 8-11mers that may be presented by MHC I.

Figure 1B:
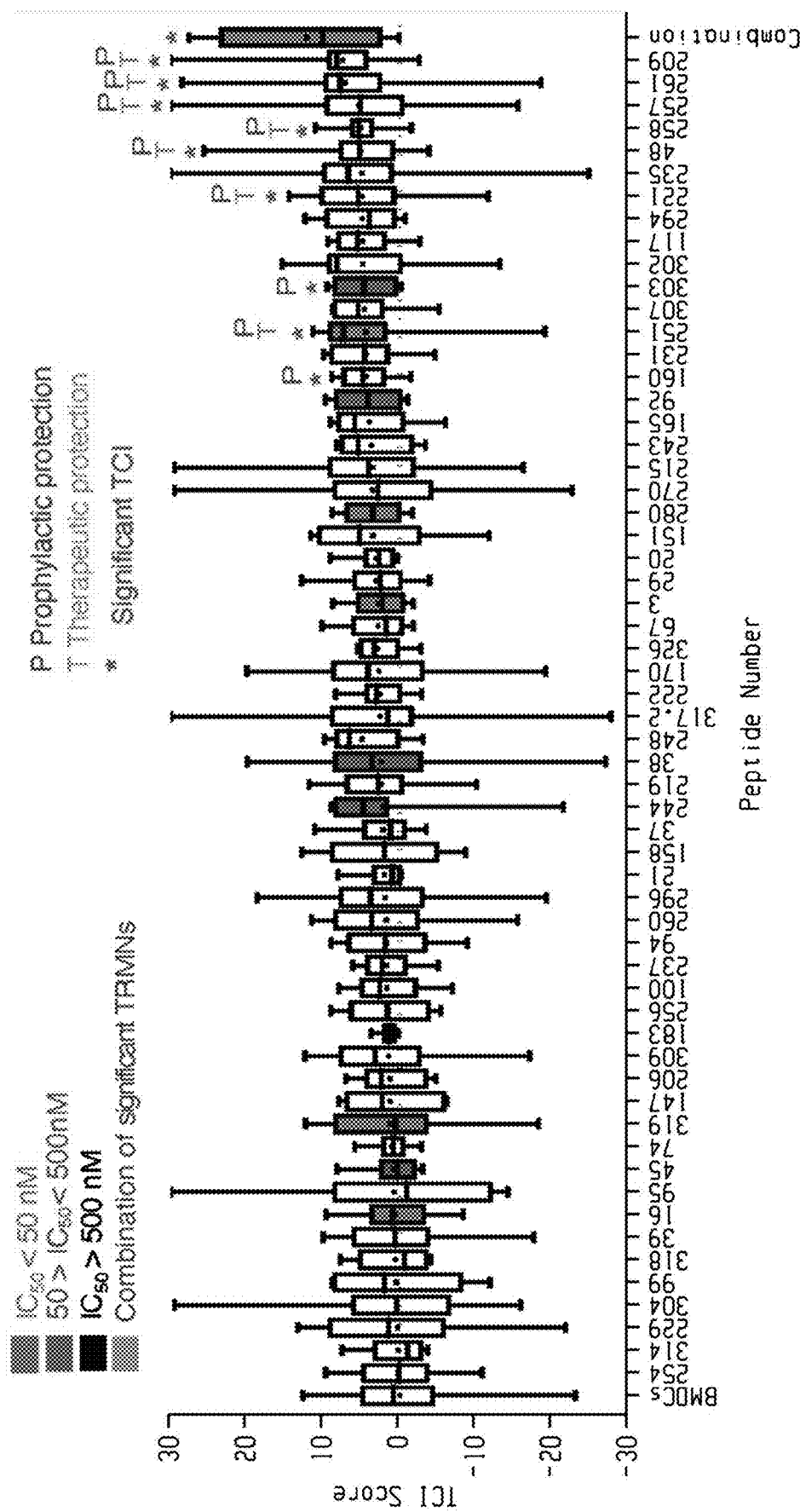

The 279 peptides were randomly grouped into 56 pools of four to five peptides per group. Mice were immunized prophylactically with each group using bone-marrow-derived dendritic cells (BMDCs) as adjuvants. In order to prevent discrepancies in peptide uptake due to competition, BMDCs were separately pulsed with each individual neoepitope from the group. The individually pulsed BMDCs were then pooled and used to immunize mice. Un-pulsed BMDCs were used as a control. All mice were challenged with 30,000 MC38-FABF cells and serial tumor measurements were converted into Tumor Control Index (TCI) scores. A higher TCI indicates better tumor rejection, tumor stabilization, or inhibition of tumor growth. Almost half the groups (24/56 groups or 42%) had a positive TCI score, even though only two groups showed statistically significant activity. Regardless of statistical significance, 120 peptides within the 24 active groups were individually tested for their capacity to elicit tumor control (FIG. 1B). Of the 120 peptides, 48% (58 peptides) showed a positive TCI score. Tumor sizes within individual groups showed considerable variation as seen in FIG. 1B. Notwithstanding this variation, about 20 peptides showed statistically significant or near significant TCI scores. These candidate active peptides were now tested in 15 to 40 mice per peptide; 9 peptides showed reproducible and statistically significant tumor control and are now referred to as TRMNs (FIG. 1B). Combination of the nine TRMNs statistically outperformed three of the nine bona fide TRMNs and trended towards better tumor control compared to the other six (FIG. 1B). In addition to prophylactic immunization, the nine TRMNs were tested for their ability to elicit therapeutic benefit in mice bearing pre-existing tumors. Seven out of nine TRMNs were active in therapy (FIG. 1B).

NetMHC4.0 was used to predict the binding affinity ($IC_{50}$) of each SNV-encoded peptide for $K^b$ and $D^b$ alleles. The 58 peptides in FIG. 1B are color-coded for the range of their affinities for $K^b$ or D&. Surprisingly, eight of nine TRMNs had an $IC_{50}$ value >500 nM (data not shown). Only one peptide (peptide 251) shows a strong-binding $IC_{50}$ value of 14.8 nM. Remarkably, if all 279 candidate peptides were screened for tumor control based on high binding to MHC I (low $IC_{50}$ values), eight of the nine TRMNs would have been excluded.

Figure 1C:
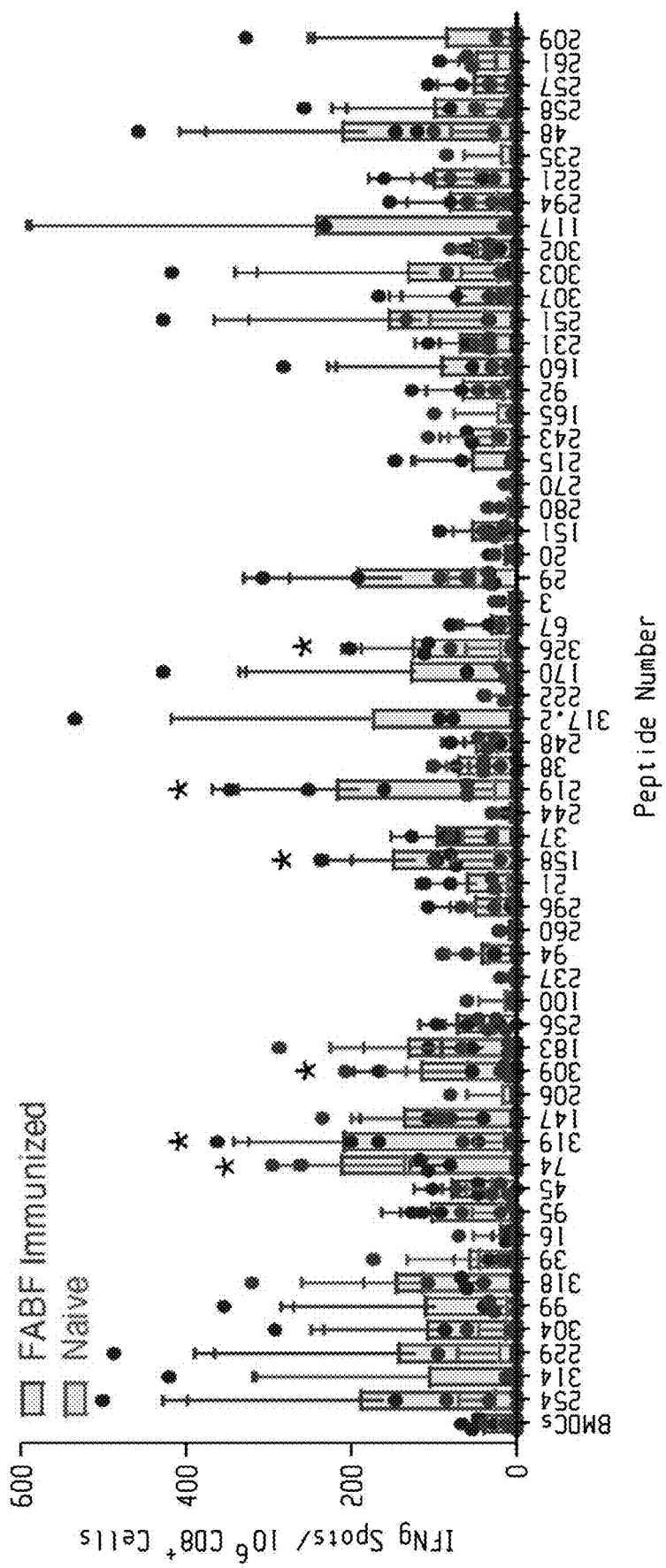

The reactivity of CD8+ T cells from mice immunized with irradiated MC38-FABF tumor cells to each of the 279 peptides was tested, and 4 peptides showed a statistically significant CD8+ response (data not shown). The CD8+ reactivity for the 58 peptides corresponding to those in FIG. 1B is shown in FIG. 1C; 4/58 peptides elicited a statistically significant positive CD8+ response. None of the TRMNs showed a statistically significant CD8+ response, and none of the 4 peptides that showed CD8*-reactivity, elicited tumor control. CD8+ T cells from mice immunized with FAM171b$^{MUT}$ and COX6a2$^{MUT}$ were also tested for cytotoxicity against MC38-FABF; however, no cytotoxicity was observed.

Figure 2A:
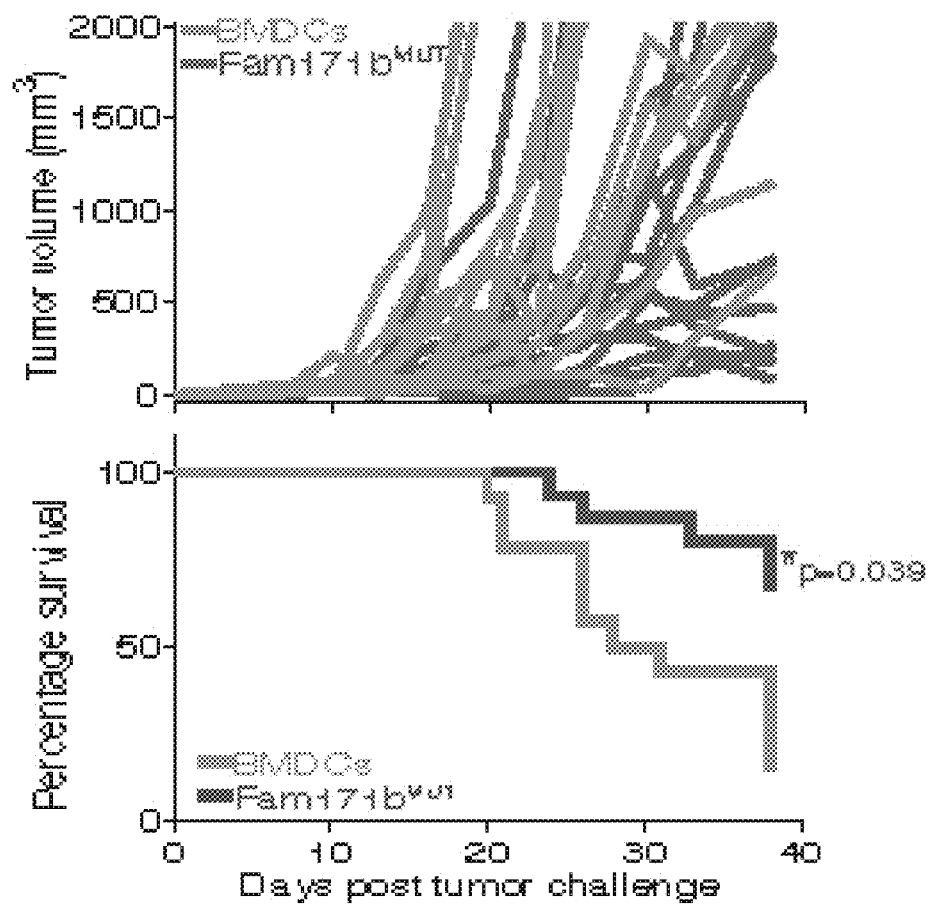
FIGS. 2A-E show characterization of the activity of TRMNs. (2A) Tumor growth curves (top) and percentage survival (bottom) of mice immunized prophylactically with FAM171b$^{MUT}$ (red) or un-pulsed BMDC (grey). Each line shows tumor volume for one mouse. The experiment was done two times (n=10, and n=5). (2B) TCI scores of mice treated with each of the nine TRMNs on days 0 and 7 post tumor challenge. Data represented as means±s.d. n=10 mice/group. Statistical analysis was performed using student's t-test; *p<0.05. The experiment was done twice. (2C) Tumor growth curves (top) and percent survival (bottom) of mice treated on days 10 and 17 post tumor challenge (indicated by arrows) with FAM171b$^{MUT}$ (red) or un-pulsed BMDC (grey), n=10 mice/group. The experiment was done twice. For survival plots (2A, B and C), statistical analysis was performed using the log rank (Mantel-Cox) test; *p<0.05. (2D) TCI scores of mice immunized with the nine TRMNs and depleted of CD8 (purple) or CD4 cells (orange) or treated with an isotype control antibody (αLTF2) (black). The experiment was done twice. Data represented as means±s.d. n=5 mice/group. Statistical analysis was preformed using 2-way ANOVA (Tukey's multiple comparisons test); *p<0.05. (2E) Mice (n=15) were immunized with un-pulsed or FAM171b$^{MUT}$-pulsed BMDCs. Five days later, CD8$^+$ cells were isolated from the inguinal and popliteal lymph nodes. Two million CD8$^+$ T cells were adoptively transferred into 9 mice/group. Mice were challenged with MC38-FABF on the right flank and MC38 on the left flank. Tumor growth was monitored. Data represent area under the curve (Top) and Growth inhibition (Bottom) in mice that received T cell transfers from un-pulsed BMDC immunized mice (Grey) or FAM171b$^{MUT}$ immunized mice (Red). *p<0.05, Students t test. Box and whisker plots were generated as in FIG. 1.
Figure 2B:
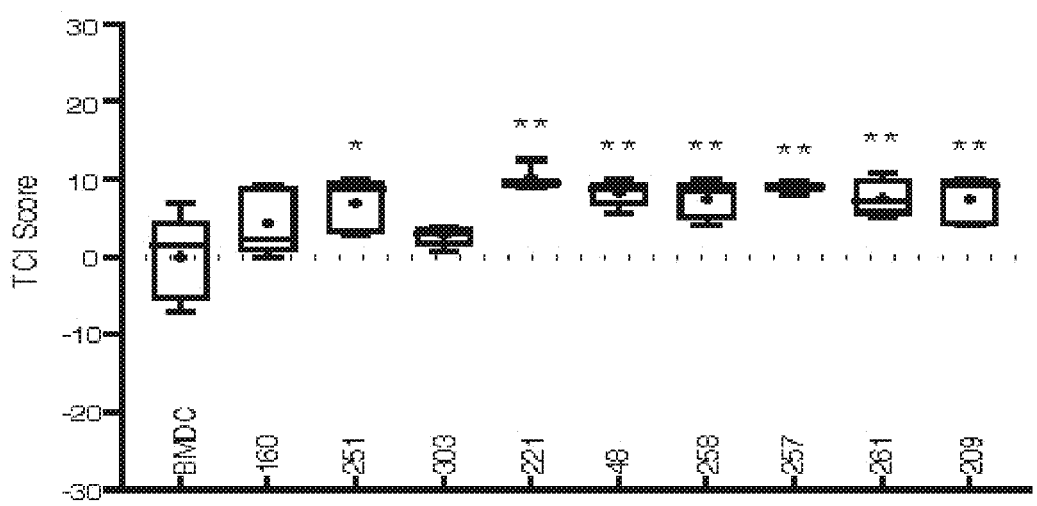
Figure 2C:
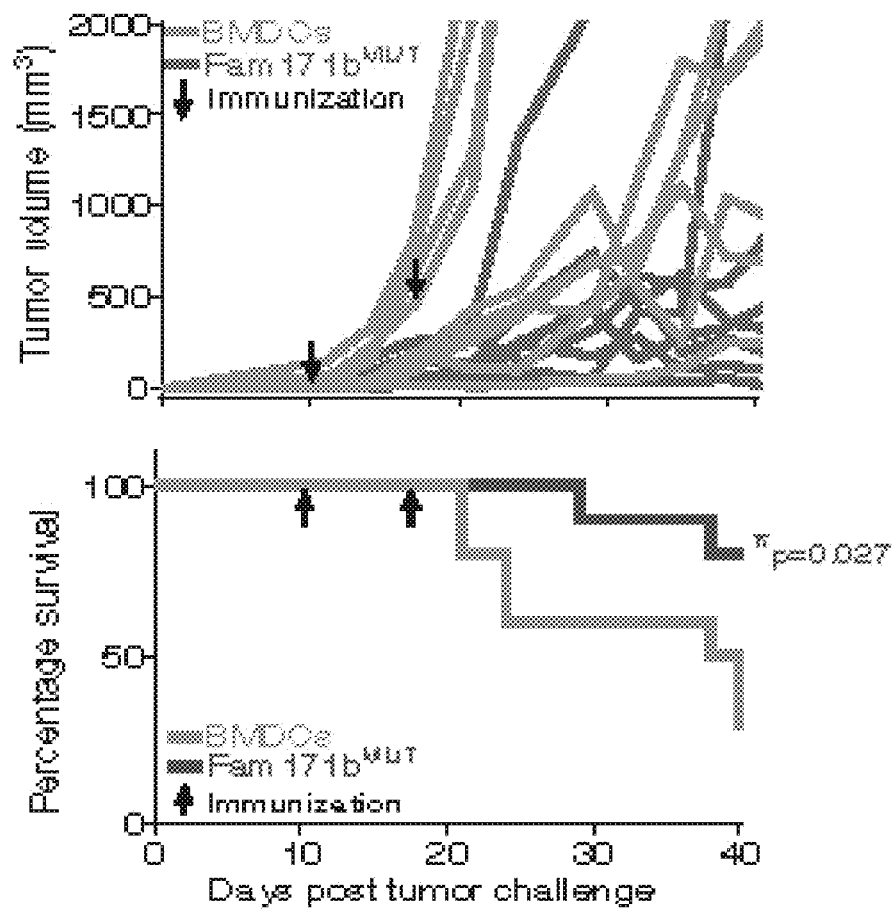
Figure 2D:
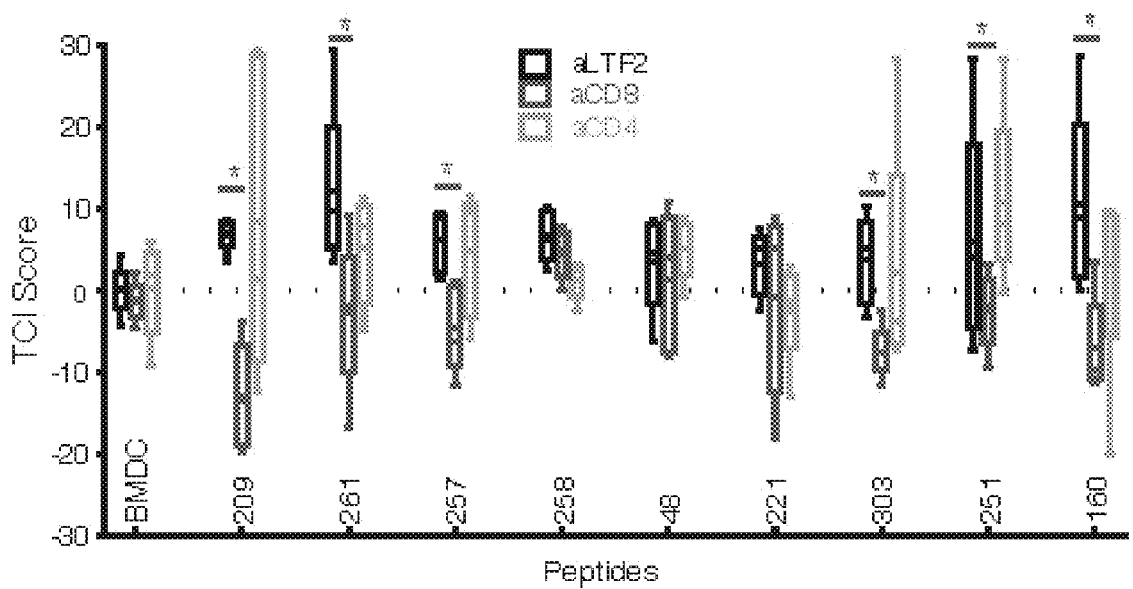

The activity of one of the strongest TRMNs, FAM171b$^{MUT}$ (peptides 209 in FIGS. 1, B and C), is shown in detail (FIG. 2A). There is a wide range of variation in the tumor growth curves in control and TRMN-immunized mice, as expected. For this reason, the tumor rejection experiments were carried out in large numbers of mice (n=10-40). Prophylactic immunization with FAM171b$^{MUT}$ elicited significant tumor control as measured by tumor growth (P<0.05), and also by survival (P=0.039), (FIG. 2A). Immunization with un-mutated peptides did not elicit tumor growth control or better survival (data not shown). All nine TRMNs were tested for efficacy when immunization was carried out on the day of tumor challenge and day 7 post tumor challenge rather than 14 days and seven days before tumor challenge (as in FIGS. 2A and data not shown); seven out of nine TRMNs elicited significant benefit in this relatively advanced setting of disease (FIG. 2B). The effect of therapeutic immunization with FAM171b$^{MUT}$ on 10-day old tumors, which are clearly visible and palpable, was tested. As seen in FIG. 2C, tumors of all mice in both groups showed nearly identical growth at the beginning of therapy; however, mice treated with FAM171b$^{MUT}$ show a significant inhibition of growth (P<0.05), and improved survival (P=0.027) (FIG. 2C). CD8+ and CD4+ T cell-dependence of the anti-tumor activity of each TRMN was tested by depletion of respective subsets in vivo; the activity of six of nine TRMNs was clearly CD8+ T cell-dependent; the data for the remaining three TRMNs were inconclusive (FIG. 2D).

Figure 2E:
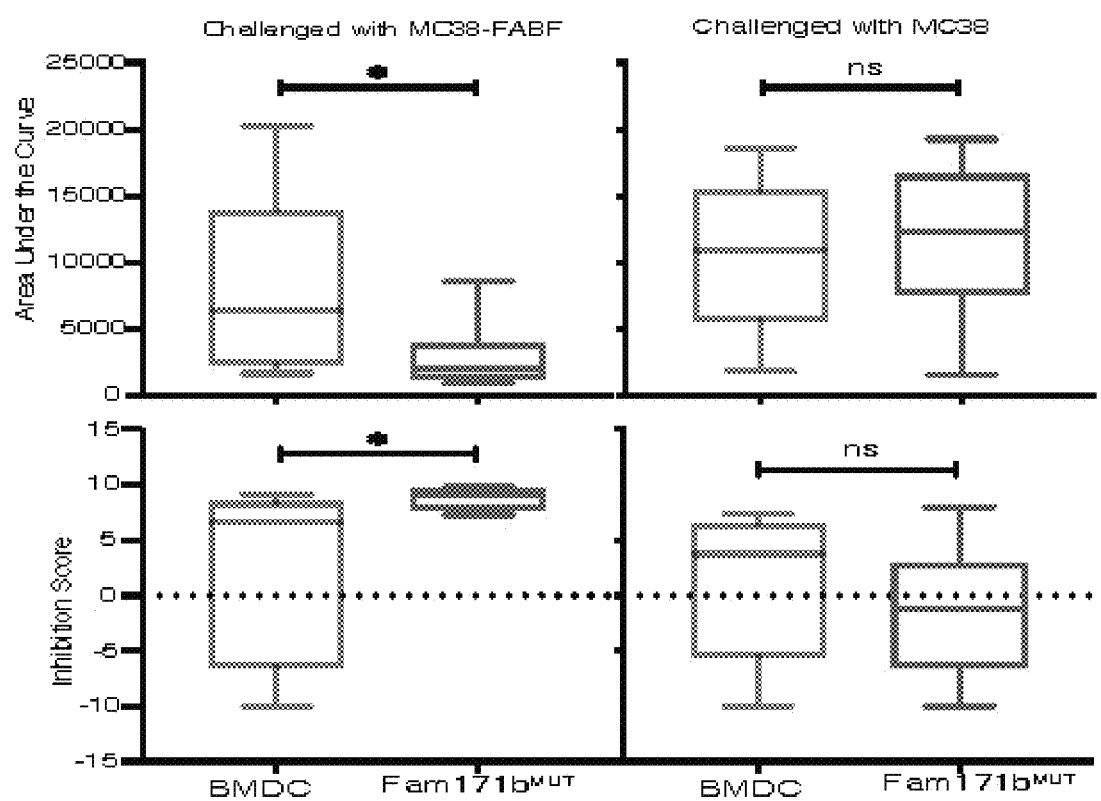

In light of the CD8-dependence of TRMN-elicited tumor immunity in the context of lack of activity of CD8+ T cells from TRMN-immunized mice in vitro in ELISpot and cytotoxicity assays, the activity of TRMN-elicited CD8+ T cells was tested in vivo in an adoptive transfer assay. Naive C57BL/6 mice were adoptively transferred with the CD8+ T lymphocytes isolated from mice that had been immunized with BMDCs alone, or with BMDCs pulsed with the active TRMN FAM171b$^{MUT}$. The recipient mice were challenged one day after the adoptive transfer on one flank with the tumor MC38-FABF, which has the mutation, and on the other flank with the MC38 line which does not have the mutation. We observe (FIG. 2E) that the growth of the MC38-FABF tumor is inhibited significantly, while the growth of the MC38 line which lacks the mutation, is not inhibited. There is no activity in mice which received CD8 lymphocytes from mice immunized with un-pulsed BMDCs.

Figure 3A:
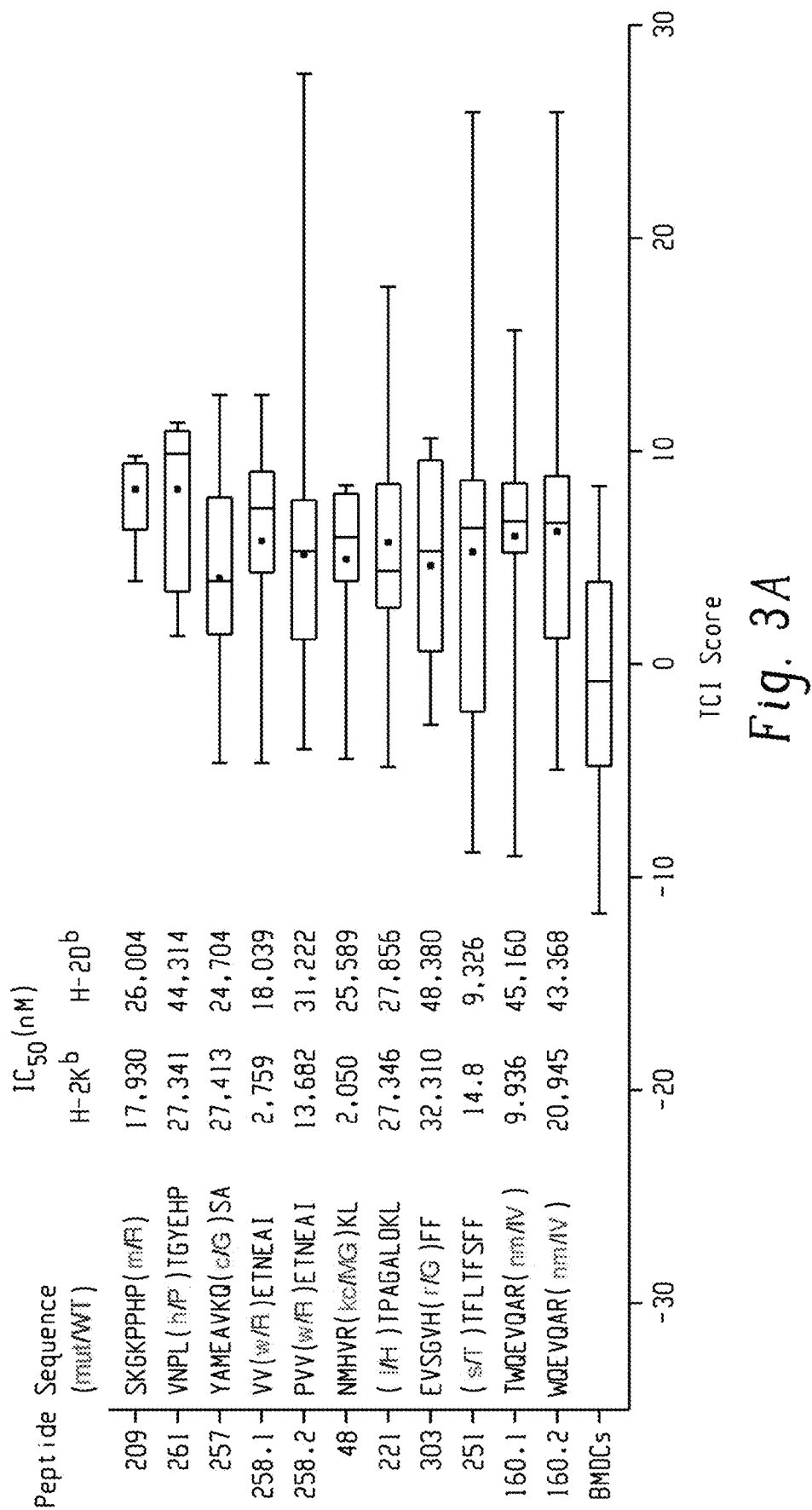
FIGS. 3A-E show the definition of precise peptides for FAM171b and COX6a2 and their interaction with cognate MHC I alleles. (3A) Sequences and binding affinities for K$^b$ and D$^b$ of the putative precise peptides of the nine TRMNs (Left; SEQ ID NOS. 1-22); TCI scores of mice immunized with precise TRMN peptides, n=15 mice/group (Right). Data represented as mean±s.d; \*p<0.05, **p<0.01 (student's t-test). (3B) Geometric MFIs of K$^b$ (Top) and D$^b$(Bottom) of RMA-S cells pulsed with precise TRMN peptides. Data represent mean of triplicate values±s.d.; statistical analysis was conducted using 2 way ANOVA. Each peptide was tested at least two times. (3C) Structural models of binding of K$^b$ with precise peptides of wild type and mutant FAM171b (SEQ ID NO: 1, 2), COX6a2 (SEQ ID NO: 4,5). The wild type is shown in green and the mutant in orange, with the MHC binding groove in grey. (3D) MS/MS mirror plot displaying similarity of overall fragment ion coverage and relative abundances of identified fragment ions between a single scan pulsed BMDC MS/MS (top pane) matched to sequence EVSGVHRFF (SEQ ID NO: 15) and the single scan MS/MS of the corresponding synthetic peptide (bottom pane). Fragment ions and neutral losses are labeled in both spectra, shared ions are shaded maroon, and singly charged (red arrows) and doubly charged ions (orange arrows) are annotated as observed for the pulsed BMDC peptide in the fragment ion coverage map. Ions represented by "•" denote those that fall within the prescribed isolation window. (3E) Left: Structural model of SH3RF bound to K$^b$. The color scheme is as in (3C). APBS electrostatic surface potentials of mutant Sh3rf1 (Top right; SEQ ID NO: 16) and wild type Sh3rf1 (Bottom right; SEQ ID NO: 16). Surface potentials are on a scale of −4.000 (blue) to +4.000 (red) $k_BTe_c^{-1}$, or ~26.7 mV per 1.000 at 310K. Box and whisker plots were generated as in FIG. 1.
Figure 3B:
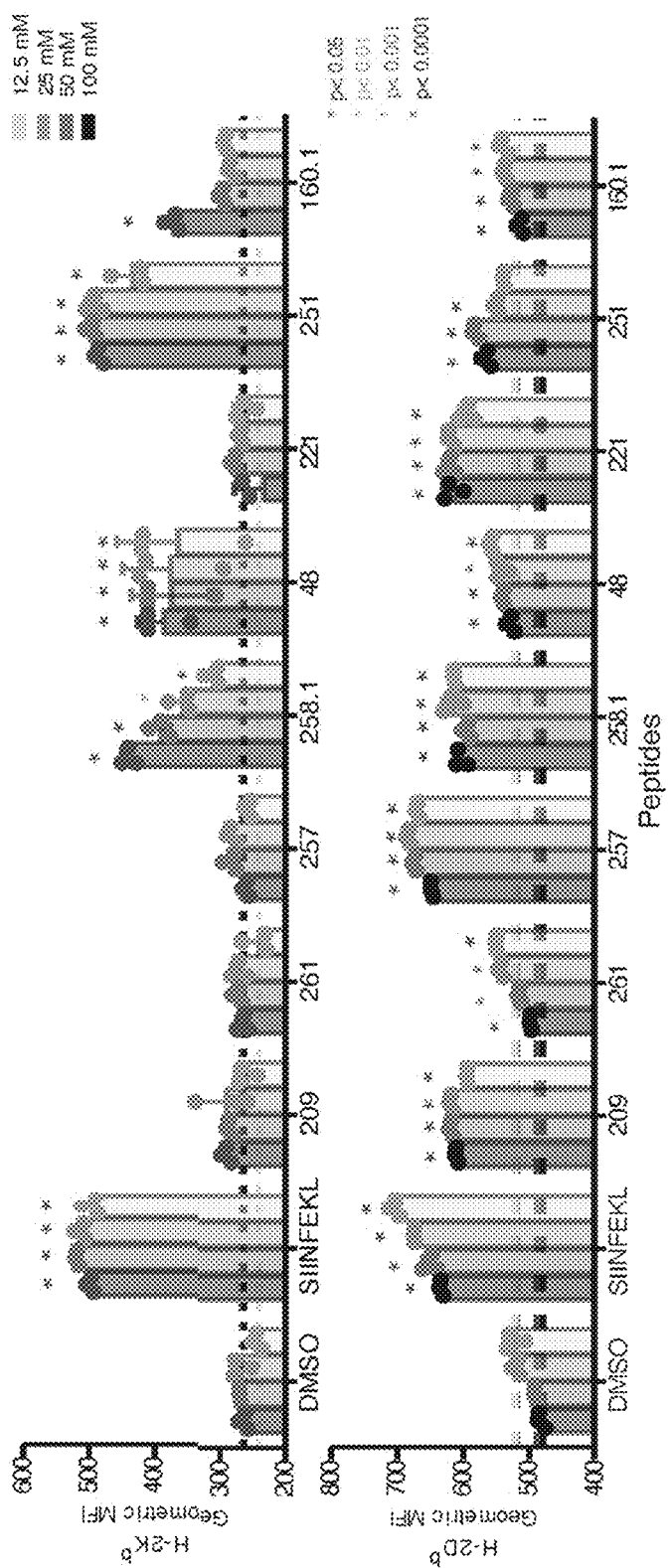

The experiments described thus far were carried out with 21-mer peptides. Next, the precise epitopes of the nine TRMNs were identified. We tested the precise peptides that had the highest predicted binding affinities to $K^b$ or $D^b$, in tumor control assays as in FIG. 1B; the TCI of each peptide is shown (FIG. 3A). Since FIG. 3A shows data on tumor control, and not antigen presentation per se, the peptides most active in tumor control in FIG. 3A were tested for their ability to pulse RMA-S cells in vitro, and stabilize pMHC I complexes recognizable by allele-specific antibodies for $K^b$ and $D^b$. Each TRMN was observed to be presented by one or both alleles (FIG. 3B). For the purpose of identification of the precise neoepitopes, the two assays (prediction by tumor rejection and stabilization of pMHC I complexes) yielded completely consistent results.

Figure 3C:
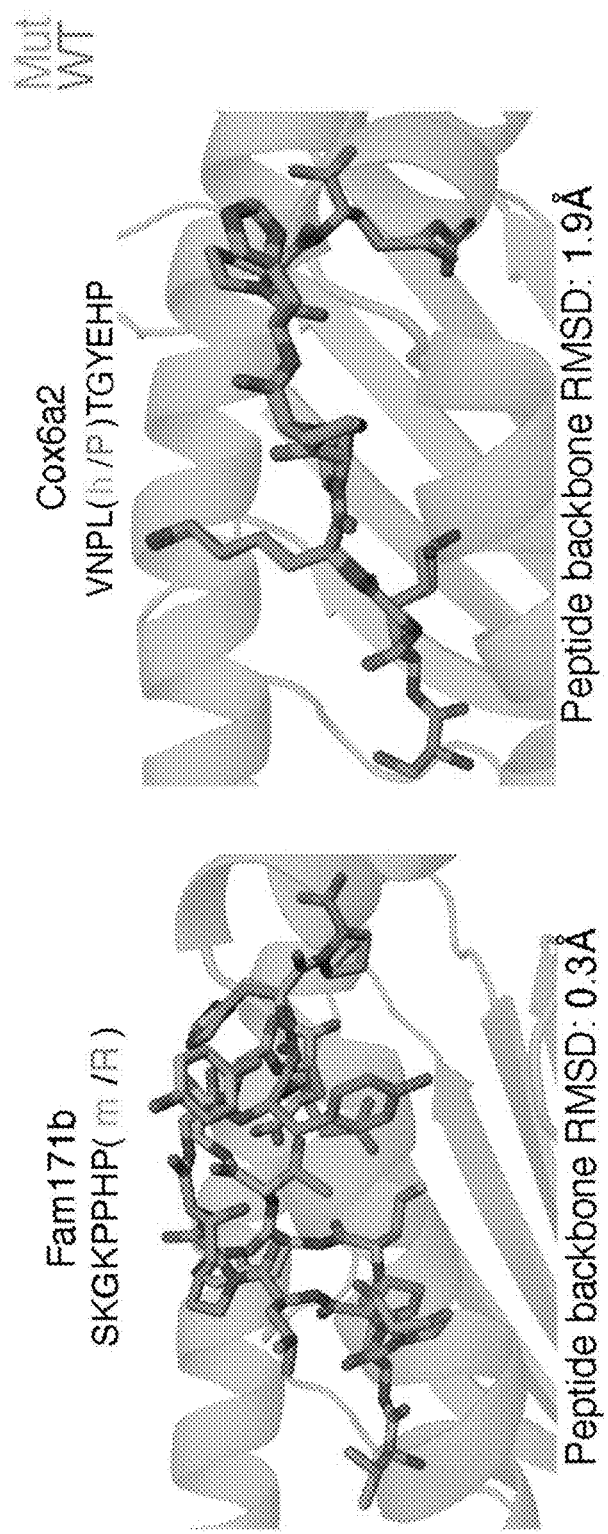
Figure 3D:
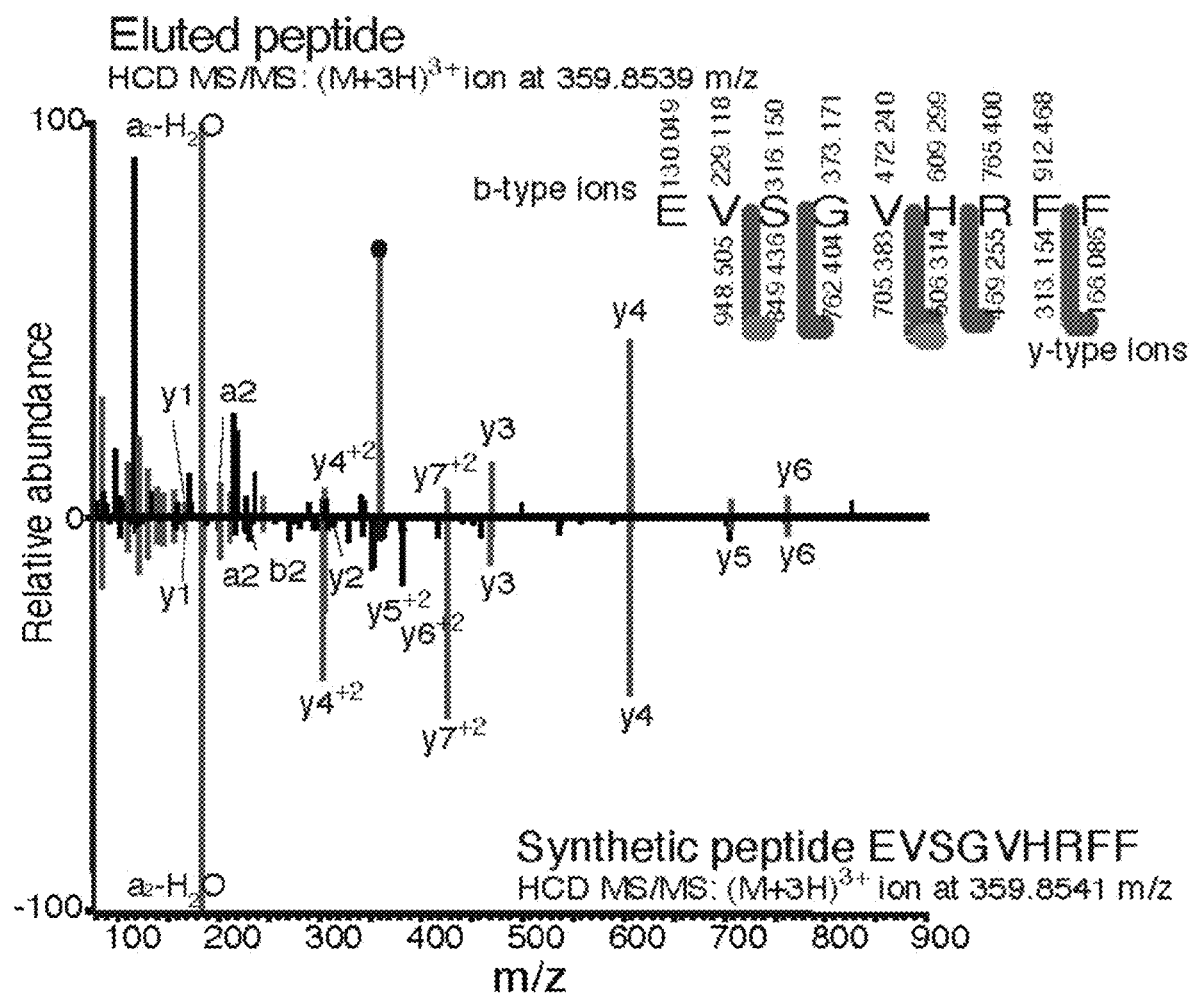

The TRMN SH3RF1$^{MUT}$ on the other hand, presents a highly illustrative example of the lack of correlation between prediction and actual presentation, and between MHC I-binding and tumor control activity. The long peptide that harbors the mutation in SH3RF1$^{MUT}$ was interrogated for prediction of binding of a precise epitope of $K^b$ or $D^b$. Of the possible candidates, peptide VHRFFPTNF (SEQ ID NO: 23) was predicted to bind $K^b$ with the highest affinity of an $IC_{50}$ of 332 nM. Interestingly, we were able to identify the precise neoepitope within the SH3RF1$^{MUT}$ long peptide by pulsing the long peptide onto BMDCs and eluting presented epitopes from the MHC I of the BMDCs (FIG. 3D). The presented neoepitope, as identified by mass spectrometry (MS), turned out to be EVSGVHRFF (SEQ ID NO: 15) which has a predicted binding affinity (to K$^b$) of 32,310 nM, two orders of magnitude lower than the predicted affinity of the strongest-binding peptide VHRFFPTNF (SEQ ID NO: 23). This observation underscores the lack of correlation between affinity for MHC I and tumor control as seen in FIG. 1B.

Example 2: Molecular Modeling of MHC Class I-Peptide Interaction

Figure 3E:
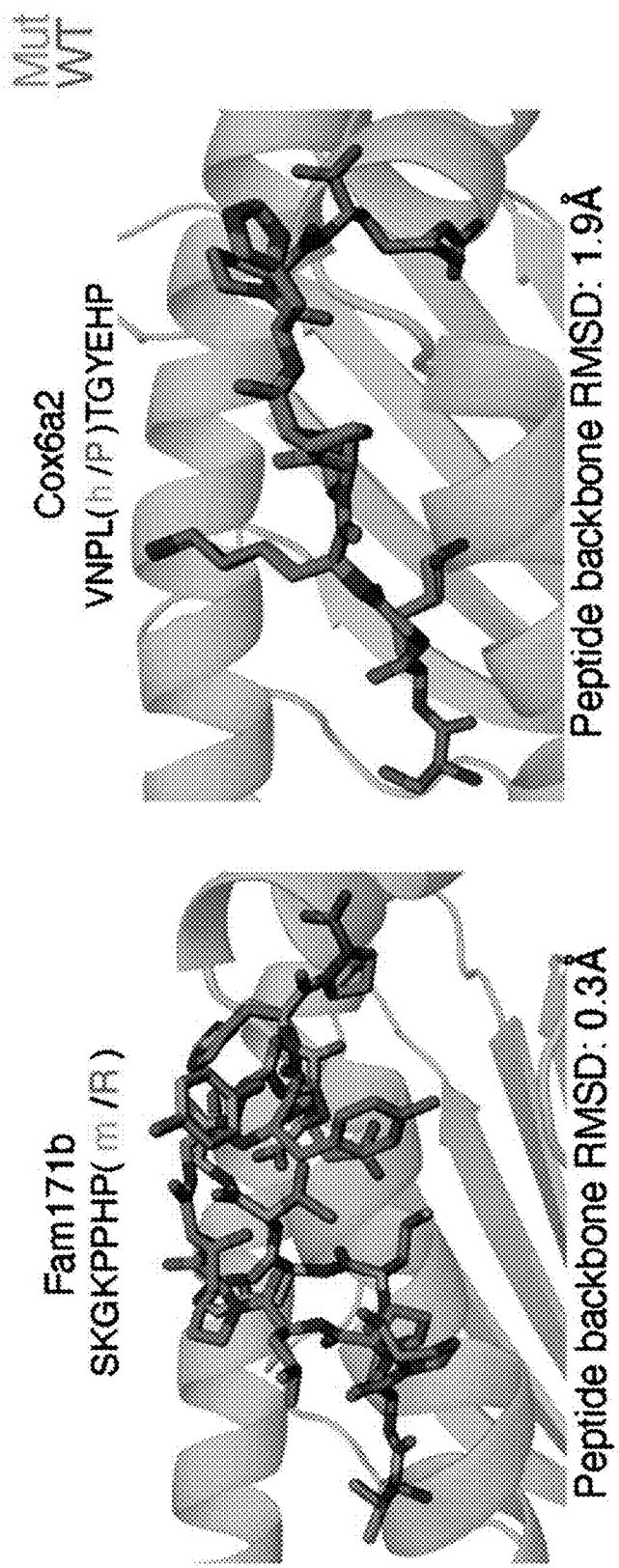

We modeled the structures of selected TRMNs and their wild type (WT) counterparts. The data on three TRMNs, COX6a2$^{MUT}$, FAM171b$^{MUT}$, and SH3RF1$^{MUT}$ bound to K$^b$ are shown since each suggests a different manner of immunogenicity of the TRMN. Models were generated using stochastic, flexible-backbone protein modeling protocols. The proline to histidine mutation at position 5 in the COX6a2$^{MUT}$ is predicted to yield a neoepitope with a substantially different conformation than the WT peptide (FIG. 3C, right). The neoepitope is predicted to adopt a more compact backbone conformation than the WT peptide in the K$^b$ binding groove, decreasing total solvent-accessible surface area (SASA) by 19% (from 484 Å$^2$ to 390 Å$^2$) and hydrophobic SASA by 28% (from 323 Å$^2$ to 232 Å$^2$). This substantial difference in peptide conformation can explain the immunogenicity of the COX6a2$^{MUT}$, as a T cell population tolerant of the WT peptide would encounter a peptide/MHC complex with substantially different surface properties. Unlike COX6a2MUT, the arginine to methionine mutation at position 9 in the FAM171b$^{MUT}$ is predicted to have no significant impact on peptide conformation when bound to K$^b$ (FIG. 3C, left). The immunogenicity of FAM171b$^{MUT}$ may stem instead from the more stable presentation of the neoepitope than its WT counterpart as in the conclusion drawn previously that a stabilizing mutation at a primary anchor position can lead to an immunogenic neoepitope by reducing the entropic cost associated with T cell receptor (TCR) binding and thus enhance receptor affinity. In the SH3RF1$^{MUT}$ peptide, the modeling predicted that the glycine to arginine mutation at position 7 of the peptide alters peptide conformation only slightly (FIG. 3E, left). However, compared to the WT peptide, the exposed surface presented to TCRs at the C-terminal end of the neoepitope is considerably altered due to the additional bulk of the arginine side chain. The change increases exposed SASA by 17% (from 322 Å$^2$ to 378 Å$^2$), and more importantly, results in the exposure of a positive charge, again contributing to a peptide whose presented surface would appear substantially different to a TCR (FIG. 3E, right).

To examine the conformational stability of these static models, we performed molecular dynamics simulations on each of the final models described above. Each model was simulated for 300 ns in explicit solvent. In general, all peptides retained their conformations throughout simulation. Only slight perturbations occurred in backbone dihedrals and side chain rotamers, supporting the conclusions drawn from the static structural models (Fig. S3A, B). The FAM171b$^{MUT}$ peptide was indeed more stable than its WT counterpart in the K$^b$ binding groove as hypothesized, at both C- and N-termini. A new insight gleaned from the molecular dynamics simulations was substantially lower conformational sampling by SH3RF1$^{MUT}$ than WT, likely owing to the glycine-to-arginine mutation. Building on the conclusions drawn from the static models, this difference in flexibility would serve to amplify the differences between the WT and mutant peptides (Fig. S3C).

Figure 4A:
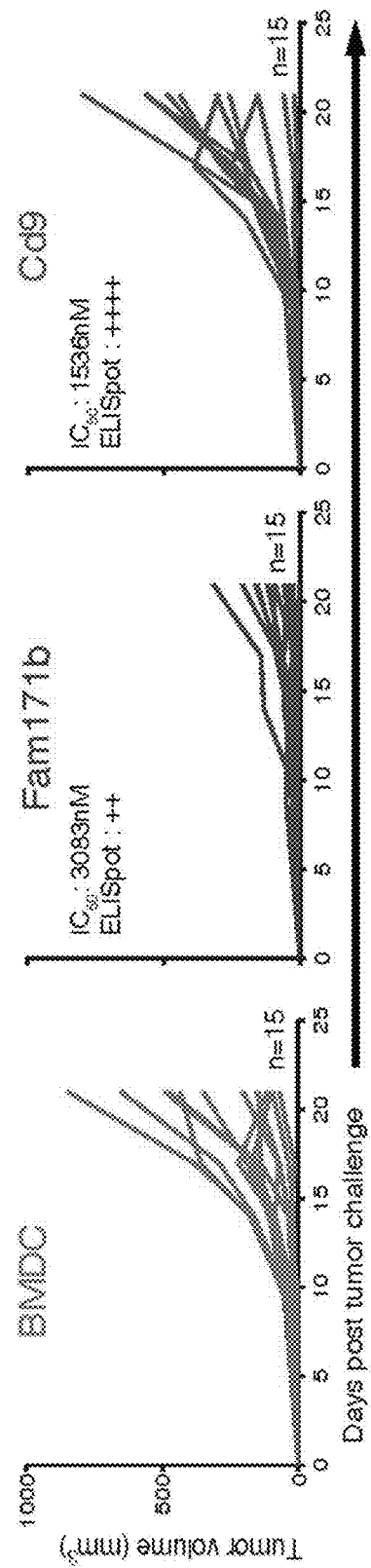
FIGS. 4A-G show phenotypes of CD8$^+$ TILs from mice immunized with a TRMN and a non-TRMN. Mice (n=15 mice per group) were immunized with un-pulsed BMDCs (green) or BMDCs pulsed with peptides FAM171b$^{MUT}$ (a TRMN, blue) or Cd9$^{MUT}$ (a non-TRMN, red) and challenged with MC38-FABF. Tumors were harvested day 25 post tumor challenge and CD8$^+$ TILs isolated. (4A) Tumor growth of mice immunized with each group. IC$_{50}$ values for cognate alleles and IFNγ ELISpot response of CD8$^+$ T cells from spleens of MC38-FABF immunized mice are indicated for each peptide (0-50 spots/10$^6$ CD8$^+$ cells=++, >140 spots/10$^6$ CD8$^+$ cells=++++). (4B) MFI of PD-1 in CD8$^+$ TILs (left); bar graph representing percentage of PD-1$^{lo}$ and PD-1$^{hi}$ cells (middle; data represented as mean f s.d with individual points); quantification of MFI of PD-1 (right). n=5 pooled mice per group, 3 technical replicates; *p<0.05, p<0.01, *p<0.001, ****p<0.0001 analyzed by ANOVA multiple comparisons test. (4C-G) Flow cytometry contour plots with indicated markers in CD8+PD-1$^+$ (low and high) TILs (left) with respective stacked bar graphs representing percentage of cells (middle) and quantification of MFI (right). Data represented as mean±s.d; n=5 pooled mice per group, 3 technical replicates; Statistics analyzed as in (4B). The data are representative of three independent experiments.
Figure 4B:
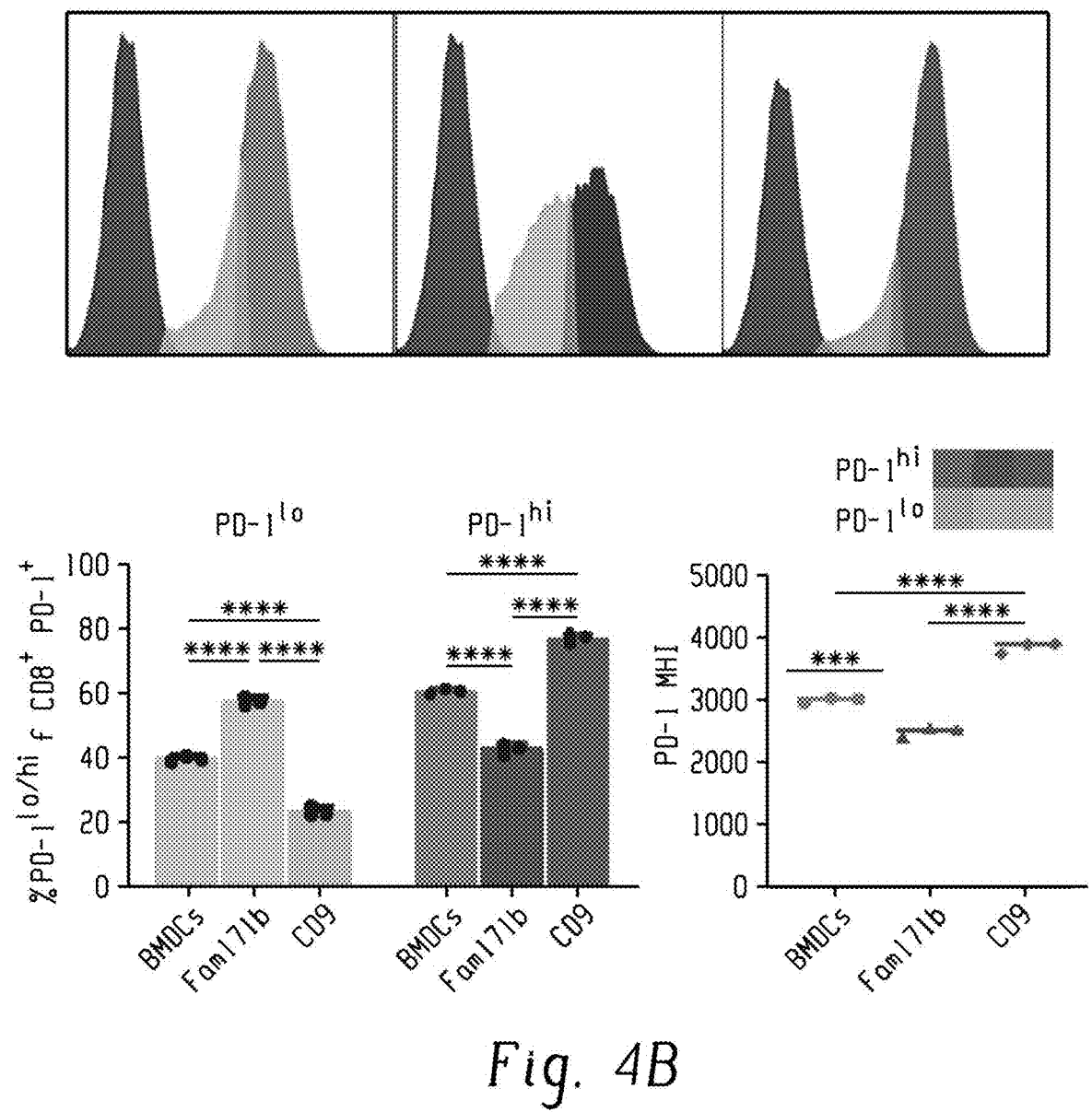
Figure 4C:
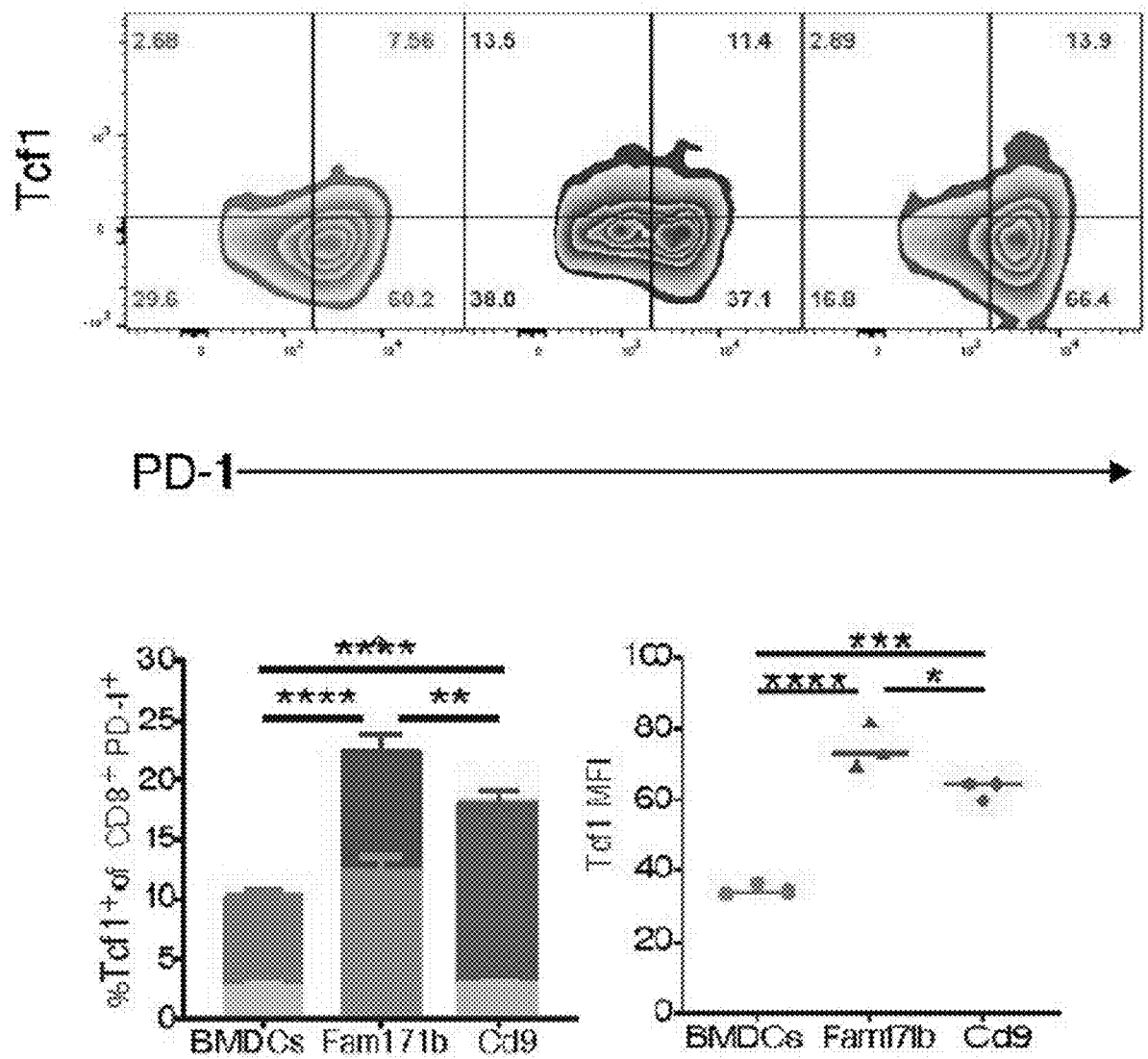
Figure 4D:
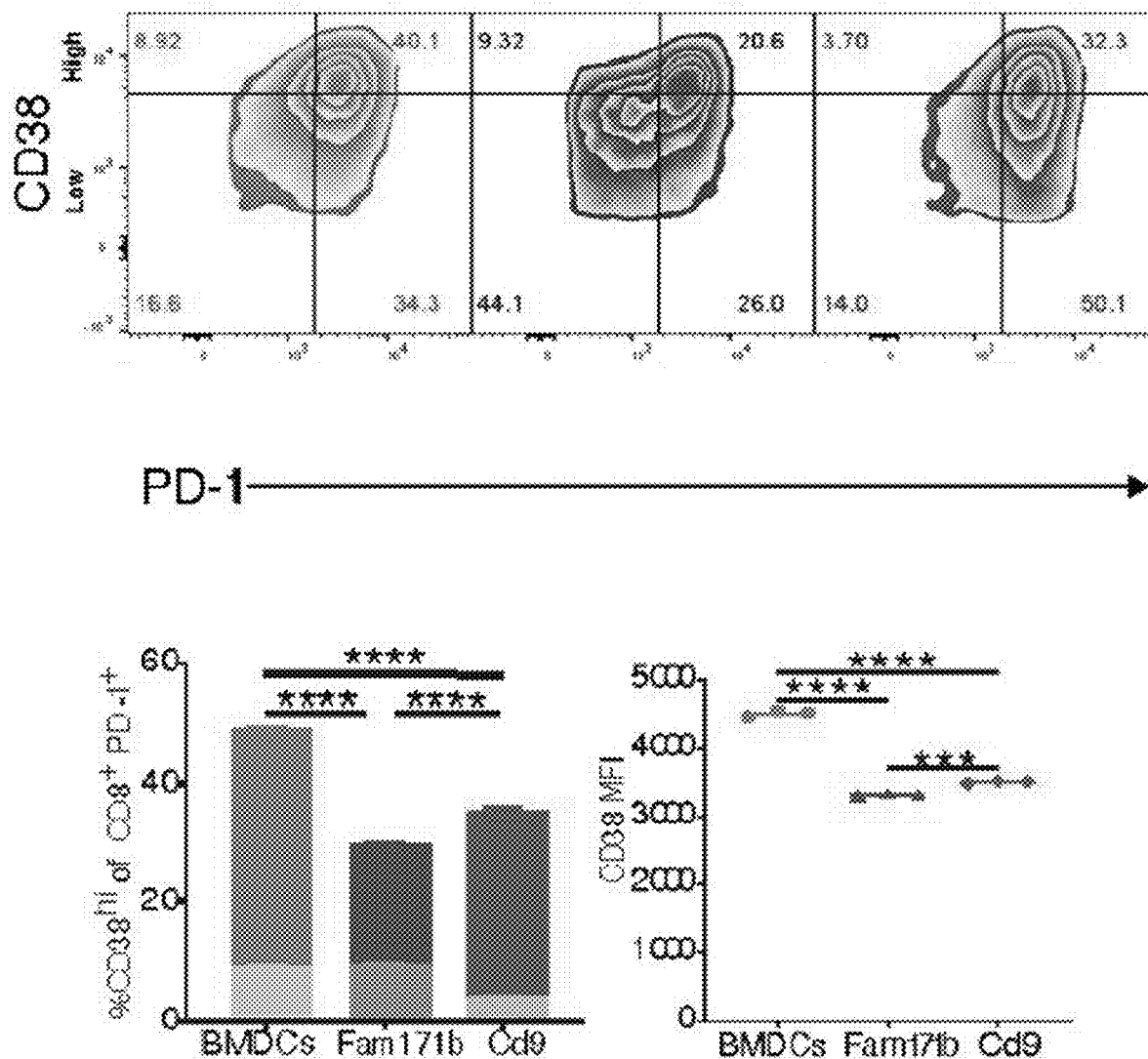
Figure 4E:
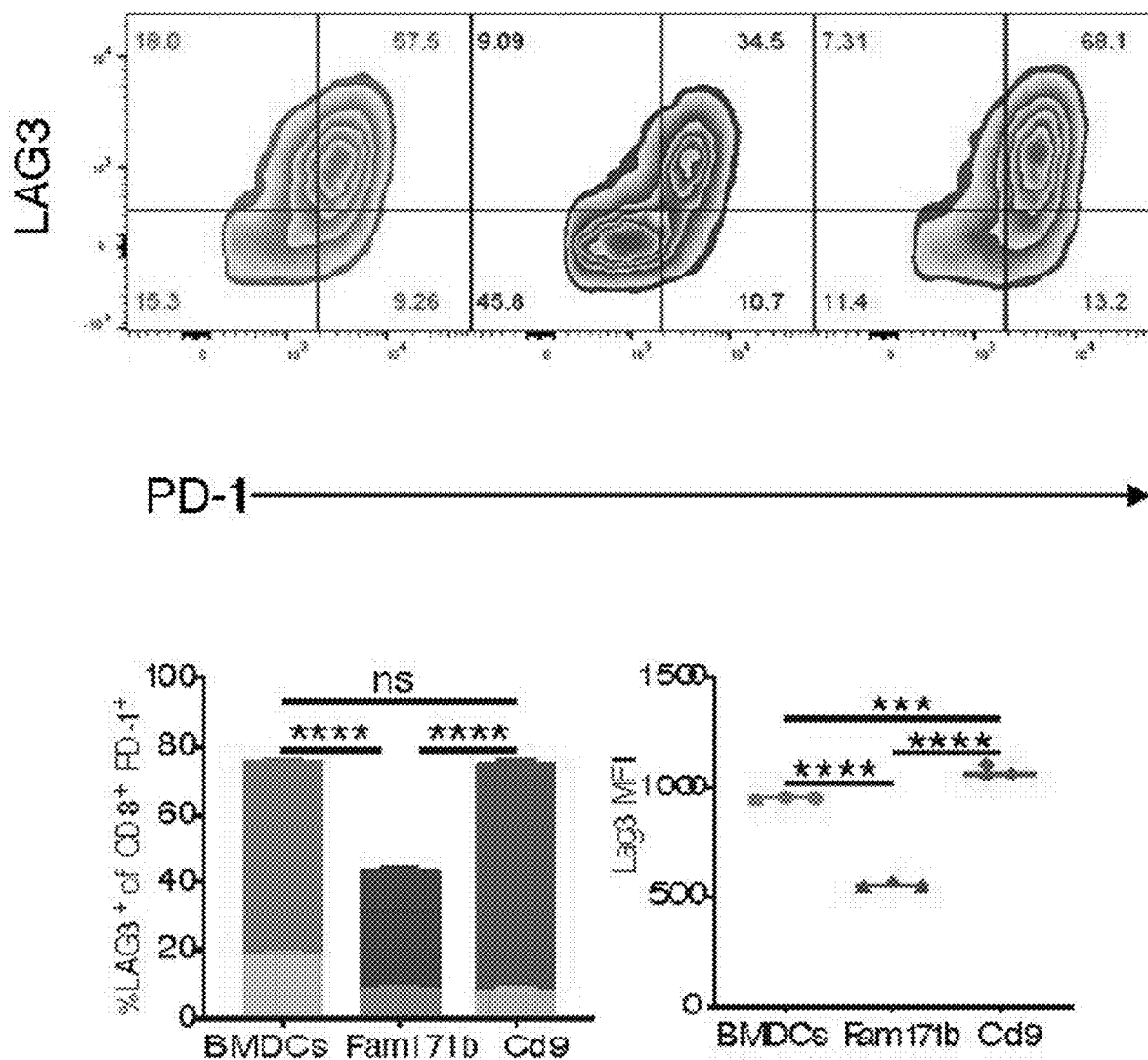
Figure 4F:
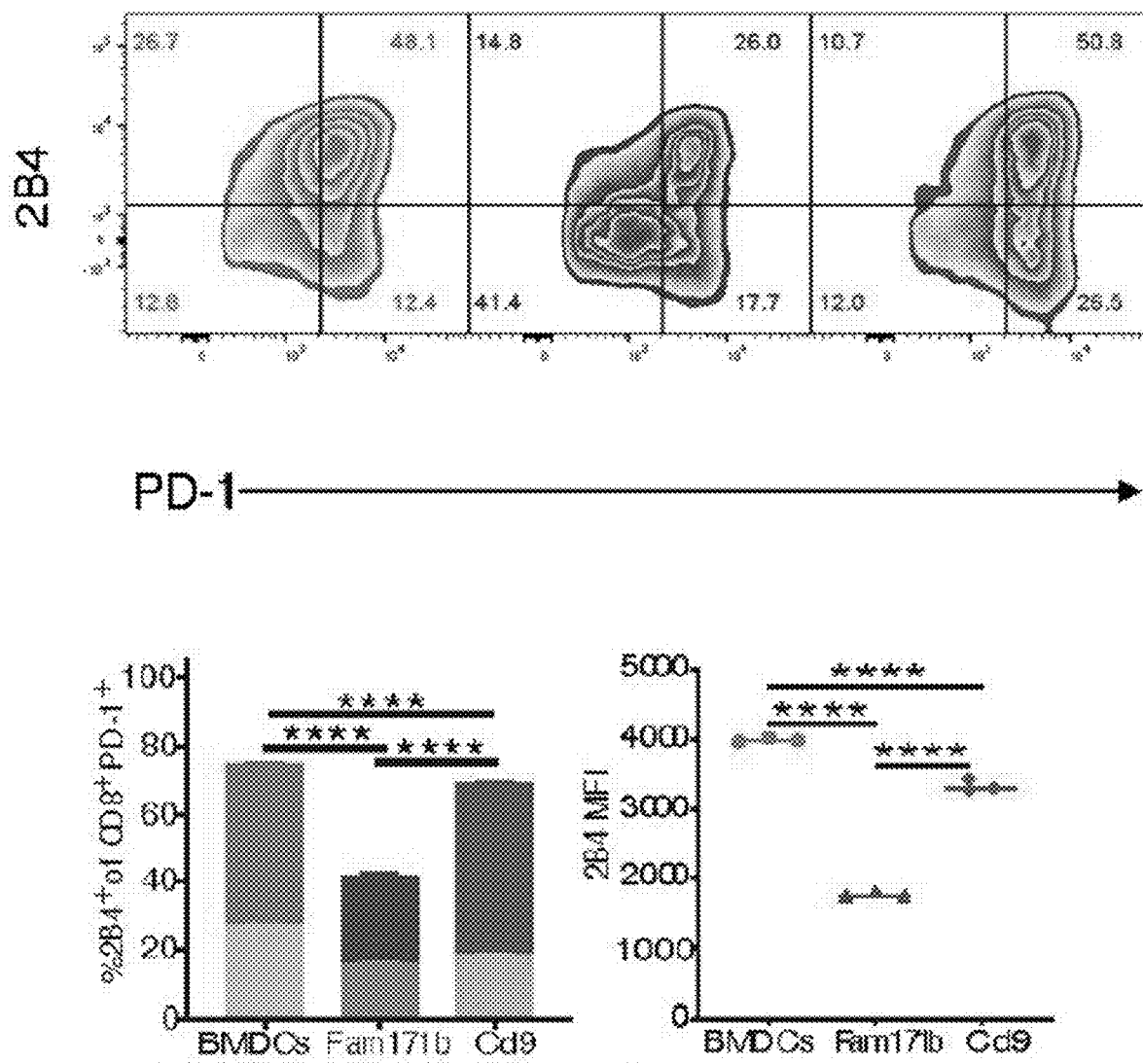
Figure 4G:
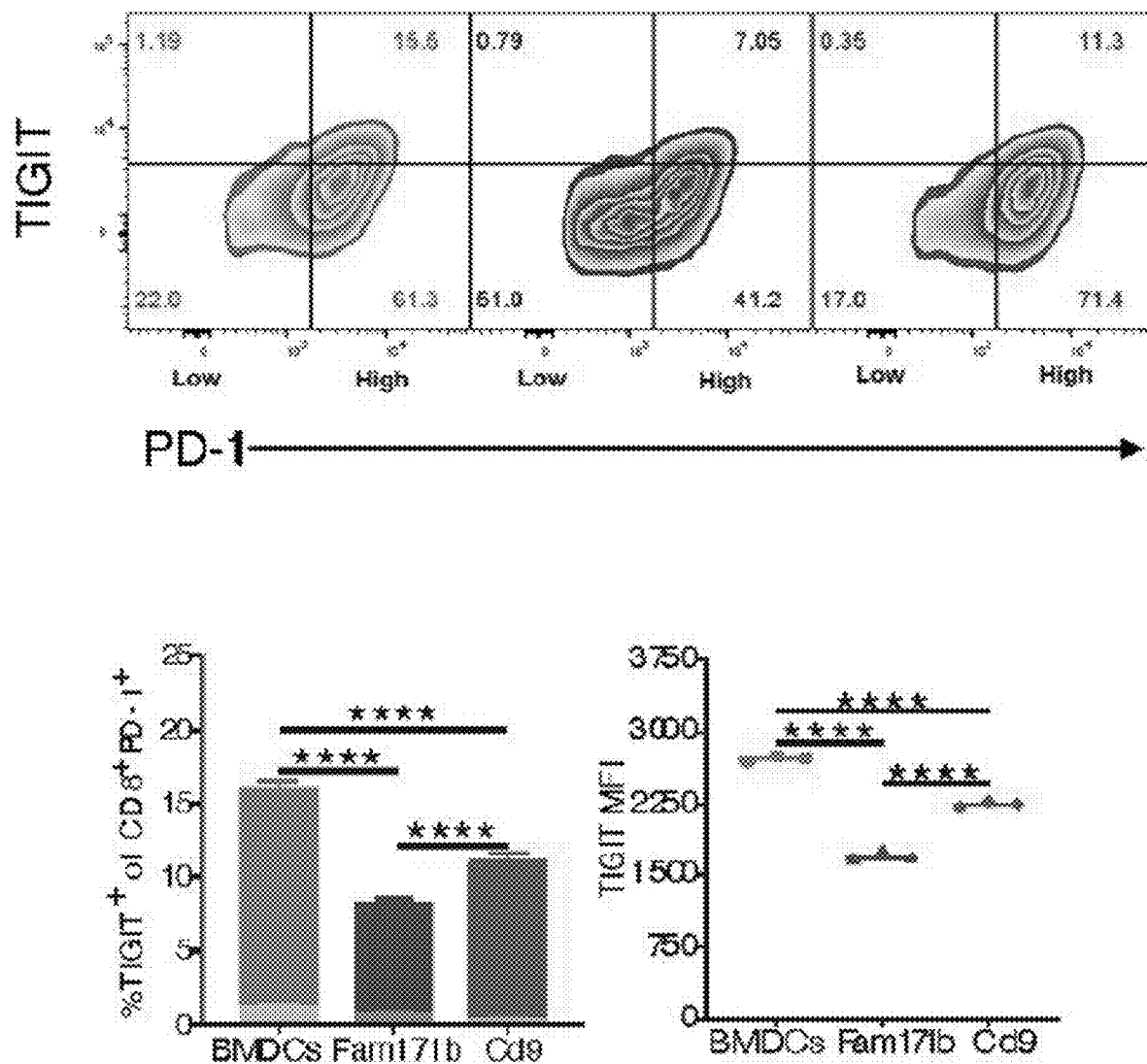

Example 3: Cd8$^+$ Tils of FAM171B$^{MUT}$-Immunized Mice have a Stem-Like Early Dysfunctional Phenotype Recent studies have shown that the effective CD8$^+$ T cell response in the context of chronic antigen exposure is mediated by CD8$^+$ T cells that have a stem-like early dysfunctional phenotype, as opposed to a terminally exhausted phenotype. The tumor infiltrating lymphocytes (TILs) from the mice immunized with a TRMN (FAM171b$^{MUT}$) and a non-TRMN (Cd9$^{MUT}$) were characterized in this regard. Mice were immunized with FAM171b$^{MUT}$ pulsed BMDCs and challenged with MC38-FABF cells; these mice show significant tumor control (FIGS. 2A and 4A) and a weak and statistically insignificant IFNγ ELISpot response (FIG. 1C and FIG. 4A). As controls, mice were immunized with un-pulsed or Cd9$^{MUT}$-pulsed BMDCs and challenged with MC38-FABF cells. Cd9mu (peptide 244 in FIG. 1C, FIG. 4A) is a mutant peptide which does not elicit tumor control but elicits statistically significant IFNγ ELISpot CD8$^+$ T cell response. Flow cytometric analysis of CD8$^+$ TILs isolated from 25-day old tumors from the three groups revealed that TILs from FAM171b$^{MUT}$ immunized mice have a unique PD-1$^{lo}$ population that is nearly absent in both control groups (FIG. 4B). This difference in PD-1 expression can be seen in the proportion of PD-1$^{lo}$ TILs as well as the MFI of total PD-1 expression among the three groups of mice (FIG. 4B). TILs from all groups contain a PD-1$^{hi}$ population, although the proportion of this population is lowest in TILs of FAM171b$^{MUT}$-immunized mice (FIG. 4B). The TILs were also analyzed for expression of Tcf1, CD38, LAG3, 2B4 and TIGIT because their expression profile have been used to described functional states of TIL, including less dysfunctional/plastic and severe dysfunction. TILs from FAM171b$^{MUT}$-immunized mice showed a higher proportion of Tcf1* cells specifically within the PD-1* population (FIG. 4C). It is also evident from the flow contour plot in FIG. 4C that the TILs from FAM171b$^{MUT}$-immunized group contain a Tcf1$^+$PD-1$^{lo}$ population that is nearly absent in the TILs of the two control groups. The MFI of Tcf1 expression by the TILs of the three groups is consistent with this interpretation. The TILs of FAM171b$^{MUT}$-immunized mice showed a lower proportion of CD38$^{hi}$ cells, as well as lower overall expression of CD38 as measured by MFI (17). The TILs of FAM171b$^{MUT}$-immunized mice also showed a lower proportion of cells expressing the co-inhibitory receptors LAG3, 2B4 and TIGIT (as well as significantly reduced MFI of these markers), than the TILs of control mice.

Figure 5A:
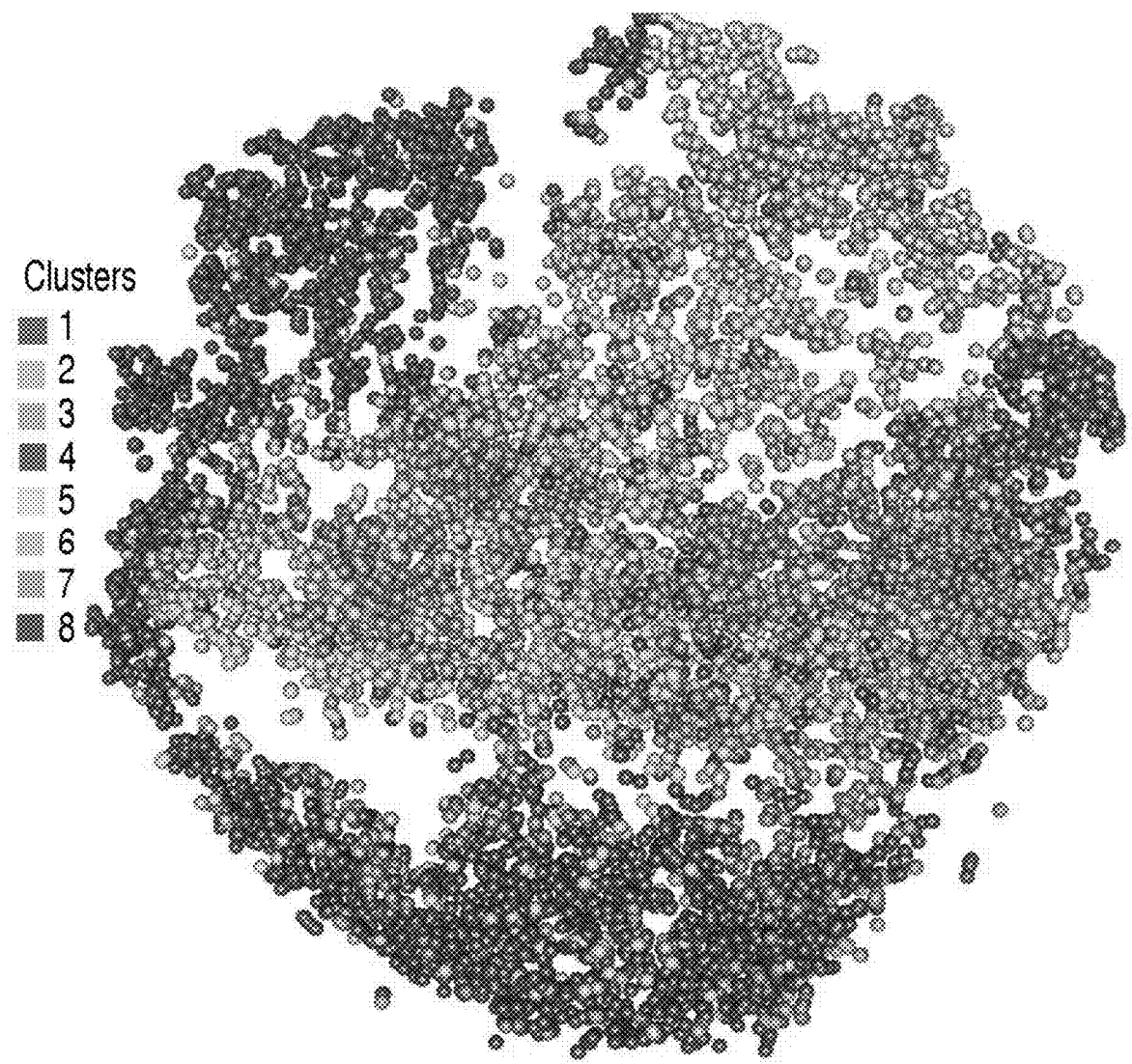
FIGS. 5A-E show single cell RNA-seq analysis of CD8$^+$ PD-1$^+$ TILs from mice immunized with a TRMN and a non-TRMN. Mice (n=3 per group) were immunized with un-pulsed BMDCs or BMDCs pulsed with peptides FAM171b$^{MUT}$ (a TRMN) or Cd9$^{MUT}$ (a non-TRMN) and challenged with MC38-FABF. Tumors were harvested day 25 post tumor challenge and live CD8$^+$PD-1$^+$ TILs isolated by fluorescence activated cell sorting (FACS) and sequenced by scRNA-seq (10× genomics). Approximately 4400 CD8$^+$ PD-1$^+$ TILs were analyzed in each library. (5A) Three-dimensional t-SNE plot showing clustering based on top average TF-IDF genes (5B) Top: Composition (distribution) plot showing percentage of cells in the 8 clusters along with respective annotations in un-pulsed BMDCs, FAM171b$^{MUT}$ and Cd9$^{MUT}$ libraries; Bottom: Table showing cluster annotation based on selected markers (5C) Summary heatmap of selected DE genes (threshold of DE as defined in Methods). (5D,E) Percentage of Tcf7 expressing cells in each of the eight clusters (5D) or in each of the three libraries as indicated (5E).
Figure 5B:
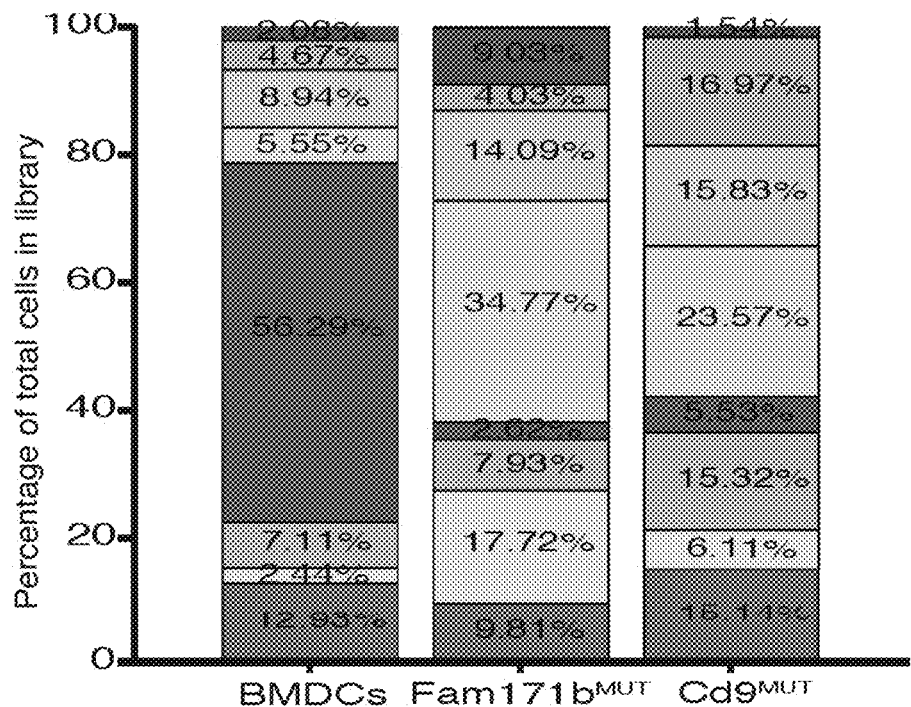
Figure 5C:
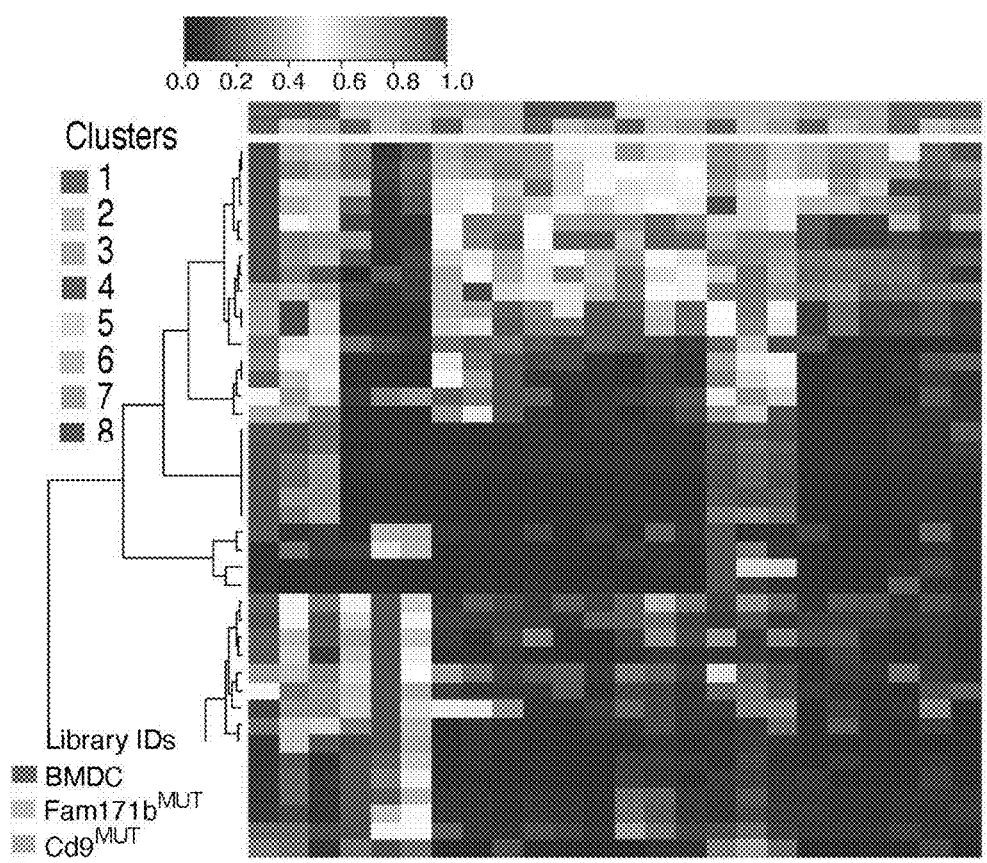
Figure 5D:
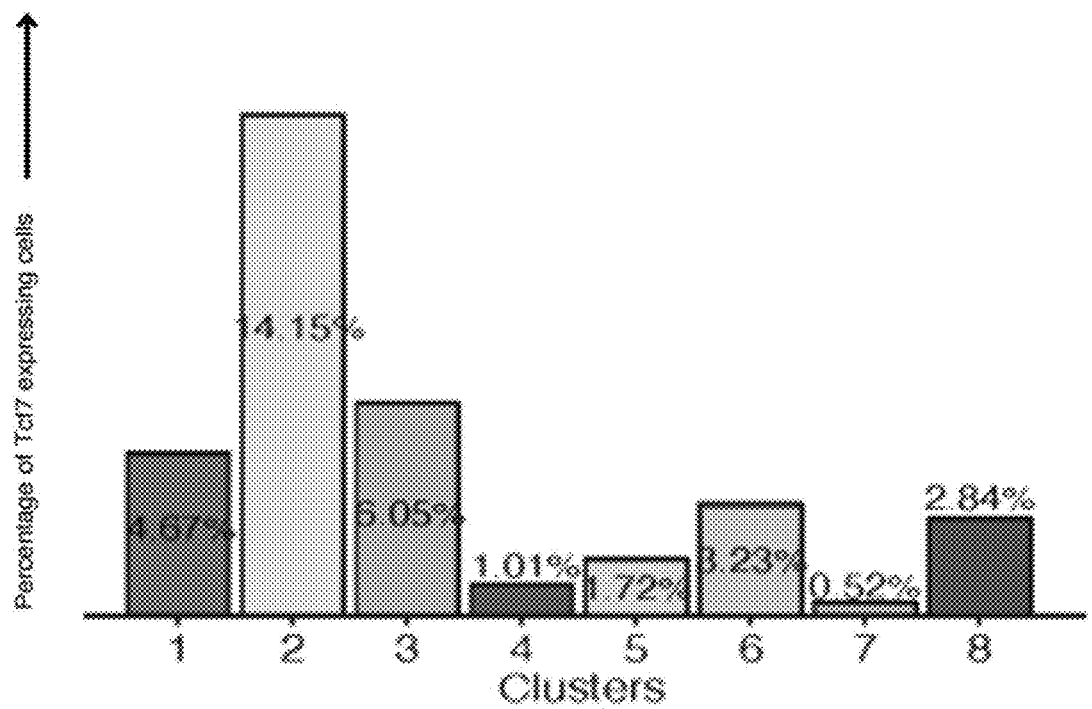
Figure 5E:
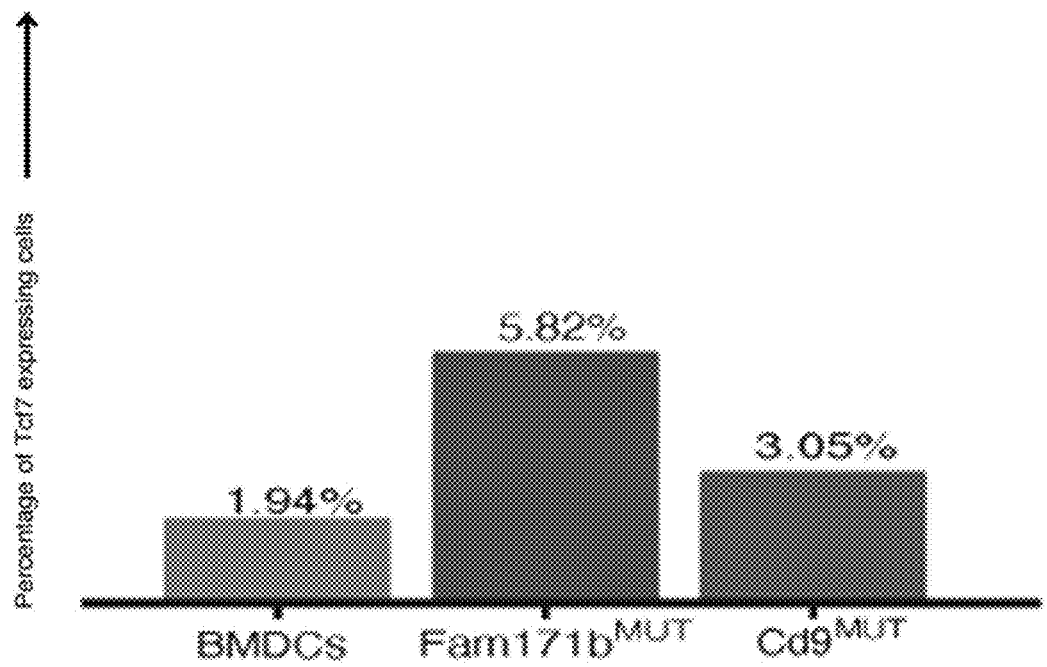

CD8$^+$PD-1$^+$ populations of TILs from the three groups were also analyzed by single cell RNA sequencing (scRNA-seq). The combined TILs from the three groups of mice resolved into eight clusters based on their transcriptional profiles (FIG. 5A). FIG. 5B shows the relative proportion of the eight cell types (clusters) among the TILs from the three groups of mice. Each of the eight clusters was annotated based on the expression of select markers and DE genes (MethodsBased on this annotation, clusters 1, 4 and 6 expressed markers of effector as well as exhausted phenotypes (FIGS. 5B and C) while cluster 3 expressed markers associated only with an effector phenotype. Cluster 7 had overall low expression of genes and hence, could not be identified. Cells in clusters 2, 5 and 8 showed expanded proportions in TILs of FAM171b$^{MUT}$-immunized mice as compared to the non-TRMN or the BMDC alone groups. Clusters 5 and 8 constituted effector cells (based on expression of Cd63, Gzme, Gzmd, Gzmc, Prf1 and Irf8, FIGS. 5B and C). Cluster 2 comprises of cells with a stem-like early dysfunctional phenotype as seen by an up-regulated expression of Tcf7(Tcf1), Itgae (CD103), Sell (CD62L), Gzmm, Lef1 and S1pr1 (FIG. 5B, C). Cells in cluster 2 also were observed to express lower levels of markers associated with exhaustion such as Tigit, Havcr2, Cd244, Tox and Ctla4. Within cluster 2, the differentially up-regulated genes are expressed at a higher level in TILs from FAM171b$^{MUT}$-immunized mice than the other two control groups (FIG. 5C). Tcf7 expression among the three groups was analyzed further (FIGS. 5, D and E). Consistent with the higher expression of Tcf7in cluster 2 (FIG. 5C), this cluster was observed to have the highest proportion of Tcf7-expressing cells among the combined TIL population of the three groups (FIG. 5D). By overall expression of Tcf7 among the TILs of the three groups of mice, Tcf7 was upregulated in FAM171b$^{MUT}$-immunized mice as compared to the other two control groups (FIG. 5E).

T cell receptors (TCRs) in the TILs of the three groups of mice were characterized using Grouping of Lymphocyte Interactions by Paratope Hotspots (GLIPH) analysis. This analysis groups together the TCRs into specificity groups based on the similarity of the CDR3 regions of the TCRs (see Methods), and shows that TILs of FAM171b$^{MUT}$-immunized mice contain a higher number of specificity groups (9 groups) than those of BMDC-immunized mice (3 groups) or Cd9$^{MUT}$-immunized mice (6 groups). In TILs of FAM171b$^{MUT}$-immunized mice, 129 distinct CDR3 sequences contributed to the largest specificity group, as opposed to 74 and 87 distinct CDR3 is consistent with increased clonality of anti-tumor TCRs in TILs of FAM171b$^{MUT}$-immunized mice (FIGS. 5, F, G and H). The largest specificity group in BMDC-immunized mice also included the most frequent clone (highest proportion of T cells with the same CDR3 sequence). In contrast, the most frequent clone in FAM171b$^{MUT}$ and Cd9$^{MUT}$-immunized mice did not belong to the largest specificity groups suggesting that a high frequency of a given clone does not necessarily correlate with the size of a specificity group.

Example 4: A Model for Enriching for TRMNS from Data in Silico

In addition to considering the affinity of a neoepitope for an MHC allele, we include in our consideration the affinity of the corresponding un-mutated peptide for the MHC allele. When neoepitopes, which are in effect, altered peptide ligands, are presented by the MHC, the affinity for these neoepitopes for an MHC allele can be the same, higher, or lower, than the corresponding affinity for the un-mutated epitope. In FIG. 6A, where the affinities for all possible mutated epitopes and their un-mutated counterparts are plotted along two perpendicular axes, the diagonal represents an equal affinity of the two counterparts for MHC. FIG. 6A shows a scatter plot of the normalized (scaled and centered) values of Mutant IC$_{50}$ (nM) on the X-axis and the Reference IC$_{50}$ (nM) on the Y-axis. Generally speaking, most points have similar affinities for un-mutated and mutated counterparts, resulting in the points being distributed symmetrically around the diagonal line. The Differential Agretopic index (DAI), a measure for difference-from-self, for neoepitopes on the diagonal (red line) is zero. Any candidate neoepitopes that fall below the diagonal have a negative DAI, and those above the diagonal, a positive DAI. In FIG. 6B, we now plot the data (normalized as described in Methods) for the nine TRMNs defined in FIG. 1B, as well as those previously published by us and others. The plot shows the bivariate scatter plot of the normalized reference and mutant IC$_{50}$ values of the peptides, with points in grey representing all negatives, while positives in various colors are grouped in three clusters: red circles in cluster 1 (7 peptides), green triangles in cluster 2 (5 peptides) and blue squares in cluster 3 (9 peptides). The number of clusters was determined by analyzing the Bayesian information criterion (BIC) and the clusters/ellipses were fit using Model-based clustering based on parameterized finite Gaussian mixture models using the reference and alternative IC$_{50}$ values as features. The dashed vertical line in FIG. 6B indicates IC$_{50}$=50 nM. The TRMNs in the individual clusters are listed in FIG. 6C. A number of patterns are clearly discernible in the three clusters: (a) cluster 3 contains TRMNs with high affinity for MHC I (IC$_{50}$ values between 2 and 157 nM) and includes TRMNs published by us in this study and as well as others. (b) cluster 2 contains TRMNs with a broader range of affinities for MHC I, with IC$_{50}$ values between 44 and 2,759 from this study and others. (c) Cluster 1 is entirely different from all previous TRMNs, and consists of seven TRMNs with extremely low MHC I-binding affinities identified in this study (IC$_{50}$ values of 17,930, 20945, 24,704, 27,341, 27,346, 32,310 nM) as well as a TRMN previously published by us (39,661 nM). Thus, cluster I represents a novel space for the existence of TRMNs, which has been revealed solely on basis of our unbiased analysis of TRMNs.

Figure 6D:
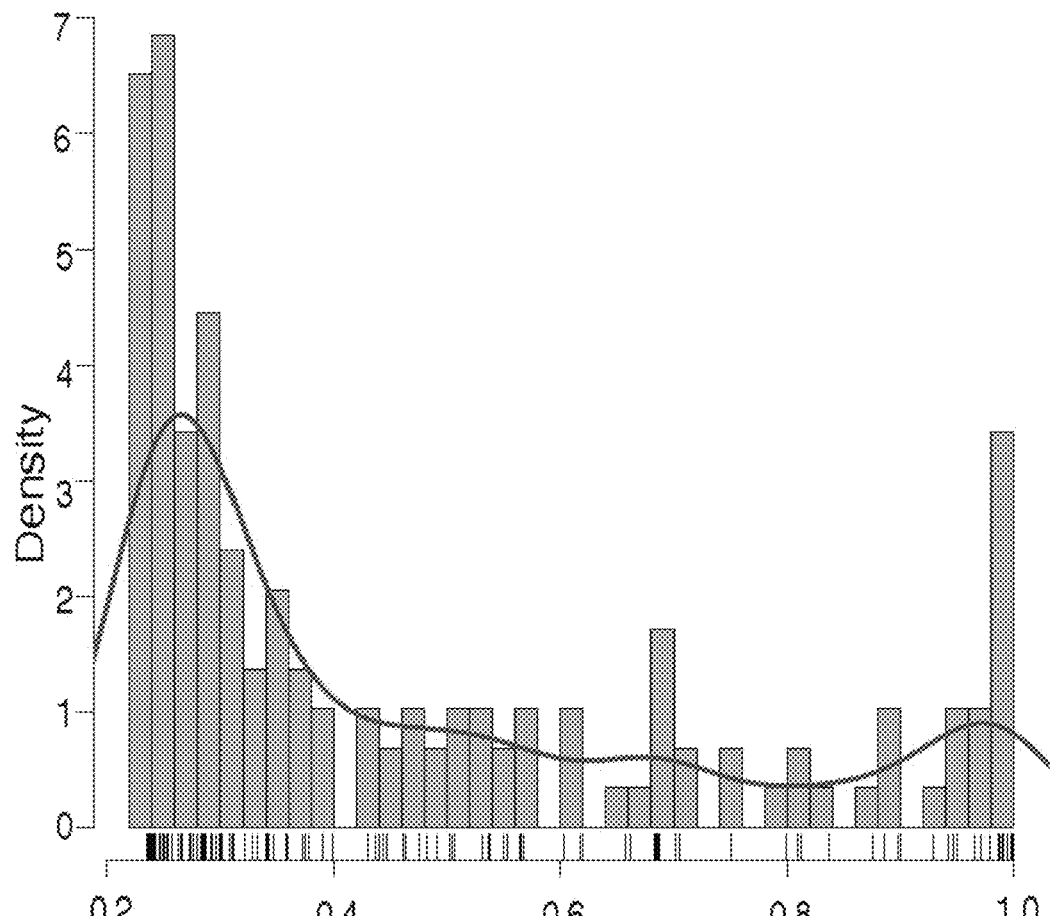

The proportion of TRMNs and non-TRMNs within each cluster has been calculated and compared. Since the true number of non-TRMN have been identified only in this study, only the data from MC38-FABF as shown here have been used in this calculation. Cluster 1 contains 6 TRMNs and 5 non-TRMNs (55% TRMNs), cluster 2 contains 2 TRMNs and 46 non-TRMNs (4% TRMNs), and cluster 3 contains I TRMN and 6 non-TRMNs (14% TRMNs). This calculation was also performed in a manner that all neoepitopes (both inside and outside the boundaries of the plotted ellipses) were forced to choose a cluster using the fitted mixture model estimation of the clusters described in FIG. 6C. By this unbiased analysis, cluster I contains 6 TRMNs and 35 non-TRMNs (15% TRMNs), cluster 2 contains 2 TRMNs and 89 non-TRMNs (2% TRMNs), and cluster 3 contains 1 TRMNs and 12 non-TRMNs (8% TRMNs). The enrichment of Cluster 1 in TRMNs is also emphasized by the fact that among all neoepitopes, the Cluster 1 is located in the lower density range of the Mutant IC$_{50}$ values described in FIG. 6D, which is under-represented as compared to the highest global density (high affinity range). These considerations demonstrate that the newly defined cluster 1 is the most highly enriched in TRMNs.

In order to test the generality of cluster 1 neoepitopes as TRMNs, we needed tumor rejection data where a sufficient number of TRMNs from a single tumor, distinct from MC38-FABF had been identified. The published data on neoepitope-mediated tumor rejection of the CMS5 tumor of a different haplotype and different tissue type (BALB/c fibrosarcoma than the C57Bl/6 colon carcinoma MC38-FABF) were the only ones to fit this criterion. In this tumor, the neoepitopes predicted by the high-affinity-binding method, which is the core of all current methods had completely failed to elicit tumor immunity: however, six neoepitopes with poor affinity for MHC I had been shown to elicit tumor rejection. We overlapped the NetMHC4 predicted Mutant and WT IC50 values of the six CMS5 TRMNs with the scatter plot from FIG. 6B preserving the same model parameters and scaling used to define the clusters described in FIG. 6B. With the exception of one outlier, all of the superimposed scaled IC50 values of the CMS5 TRMNs fall within the boundaries or closely adjacent to Cluster I (data not shown), which was learned solely using MC38-FABF data.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. "About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within 10% or 5% of the stated value. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. An unbiased method of identifying tumor rejection mediating neoepitopes (TRMNs), comprising:
   comparing a cancer cell exome sequence from a cancer patient to a reference exome sequence and identifying single nucleotide variants (SNVs) in the cancer cell exome sequence compared to the reference exome sequence;
   validating the SNVs using nucleic acid sequencing;
   identifying 8-14 amino acid putative neoepitopes including the validated SNVs, wherein the putative neoepitopes are unbiased by MHC binding and/or CD8T* reactivity;
   calculating an $IC_{50}$ for an MHC allele for each 8-14 amino acid putative neoepitope including the SNVs and calculating an $IC_{50}$ for the MHC allele for a corresponding non-mutated amino acid sequence for each validated SNV;
   plotting the putative neoepitope $IC_{50}$s on one axis, and the non-mutated amino acid sequence $IC_{50}$s on a perpendicular axis to provide a bivariate scatter plot;
   clustering the putative neoepitopes in the bivariate scatter plot using model-based clustering based on parameterized finite Gaussian mixture models using the $IC_{50}$s;
   selecting as TRMNs the neoepitopes in the bivariate scatter plot which are clustered putative neoepitopes in the space greater than 501 nM on the x-axis and greater than 501 nM on the y-axis
   wherein the TRMNs are in an elliptical cluster encompassed by a circle having a center at 27,176.9 nM for the x-axis and 33,556.51 nM for the y-axis, and a radius of 33,195 nM from the center, or
   wherein the TRMNs are in an elliptical cluster encompassed by a circle having a center at 27,176.9 nM for the x-axis and 33,556.51 nM for the y-axis and a radius of 22,430 nM from the center;

producing a peptide population or a nucleic acid population for expressing the peptide population, the peptide population comprising 15-100 different amino acid peptides, the peptides including one or more of the TRMNs;

producing a pharmaceutical composition comprising a pharmaceutically acceptable carrier and the peptide population or nucleic acid population; and optionally administering the pharmaceutical composition to the cancer patient.

2. The method of claim 1, further comprising normalizing the putative neoepitope $IC_{50}$s and the non-mutated amino acid sequence $IC_{50}$s prior to plotting.

3. The method of claim 1, wherein the TRMNs have $IC_{50}$ values for the MHC allele of 2,000 nM to 33,000 nM.

4. The method of claim 1, wherein the TRMNs do not produce a statistically significant $CD8^+$ T cell response, measured by ELISpot, cytotoxicity or FACS assays.

5. The method of claim 1, wherein NetMHC 4.0 is used to determine the $IC_{50}$s for the MHC allele.

6. The method of claim 1, wherein the cancer cell exome sequence is from cancer cells that are solid tumor cancer cells.

7. The method of claim 6, wherein the solid tumor cancer cells are from breast, prostate, ovaries, lungs or brain, and the liquid cancer cells are from a leukemia or a lymphoma.

8. The method of claim 1, wherein the cancer cell exome sequence includes all potential neoepitopes in the cancer cells.

9. The method of claim 1, wherein the reference exome is from a subject of the same species as the cancer cells.

10. The method of claim 1, wherein the pharmaceutical composition further comprises an adjuvant.

11. The method of claim 1, wherein the pharmaceutical composition further comprises one or more immune-modulating agents.

12. The method of claim 11, wherein the immune-modulating agent is a TLR ligand or an antibody.

13. A method of treating a cancer patient comprising identifying an unbiased population of tumor rejection mediating neoepitopes (TRMNs) by;

comparing a cancer cell exome sequence from the cancer patient to a reference exome sequence and identifying single nucleotide variants (SNVs) in the cancer cell exome sequence compared to the reference exome sequence;

validating the SNVs using nucleic acid sequencing;

identifying 8-14 amino acid putative neoepitopes including the validated SNVs, wherein the putative neoepitopes are unbiased by MHC binding and/or CD8T* reactivity;

calculating an $IC_{50}$ for an MHC allele for each 8-14 amino acid putative neoepitope including the SNVs and calculating an $IC_{50}$ for the MHC allele for a corresponding non-mutated amino acid sequence for each validated SNV;

plotting the putative neoepitope $IC_{50}$s on the x-axis, and the non-mutated amino acid sequence $IC_{50}$s on the y-axis to provide a bivariate scatter plot;

clustering the putative neoepitopes in the bivariate scatter plot using model-based clustering based on parameterized finite Gaussian mixture models using the $IC_{50}$s selecting as TRMNs the neoepitopes in the bivariate scatter plot which are clustered putative neoepitopes in the space greater than 501 nM on the x-axis and greater than 501 nM on the y-axis wherein the TRMNs are in an elliptical cluster encompassed by a circle having a center at 27,176.9 nM for the x-axis and 33,556.51 nM for the y-axis, and a radius of 33,195 nM from the center, and/or wherein the TRMNs are in an elliptical cluster encompassed by a circle having a center at 27,176.9 nM for the x-axis and 33,556.51 nM for the y-axis and a radius of 22,430 nM from the center;

producing a peptide population or a nucleic acid population for expressing the peptide population, the peptide population comprising 15-100 different amino acid peptides, the peptides including one or more of the TRMNs;

producing a pharmaceutical composition comprising a pharmaceutically acceptable carrier and the peptide population or nucleic acid population; and administering the pharmaceutical composition to the cancer patient.

* * * * *